United States Patent [19]
Murakami et al.

[11] 4,041,032
[45] Aug. 9, 1977

[54] PYRAZINE DERIVATIVES

[75] Inventors: Masuo Murakami; Kozo Takahashi, both of Tokyo; Yasuhumi Hirata, Ageo; Mutsuo Takashima, Kawagoe; Masaaki Takeda, Urawa; Hiroyoshi Ino; Sumio Iwanami, both of Ageo, all of Japan

[73] Assignee: Yamanouchi Pharmaceutical Co., Ltd., Tokyo, Japan

[21] Appl. No.: 534,636

[22] Filed: Dec. 19, 1974

[30] Foreign Application Priority Data
Jan. 16, 1974 Japan .................. 49-7726
Apr. 16, 1974 Japan .................. 49-43027

[51] Int. Cl.² ........................... C07D 241/28
[52] U.S. Cl. .................. 260/250 BN; 424/250; 544/120; 544/121; 544/82
[58] Field of Search ...... 260/250 BN, 268 C, 247.2 A

[56] References Cited
U.S. PATENT DOCUMENTS
3,544,568  12/1970  Cragoe et al. .............. 260/250 R X Primary Examiner—Donald G. Daus
Assistant Examiner—D. B. Springer
Attorney, Agent, or Firm—Burgess, Ryan and Wayne

[57] ABSTRACT

Pyrazine derivatives by the formula

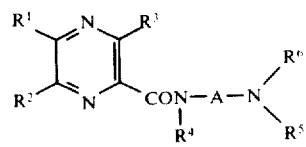

are disclosed. In the above formula, $R^1$ and $R^2$, which may be the same or different, each represents a hydrogen atom, a halogen atom, a hydroxy group, a lower alkoxy group, a phenyl lower alkoxy group, a phenoxy group, a mercapto group, a lower alkylthio group, a phenyl lower alkylthio group, a phenylthio group, an amino group, a substituted amino group, a lower alkyl group, a carbamoyl group or a sulfamoyl group; $R^3$ represents a lower alkoxy group; $R^4$, $R^5$, and $R^6$, which may be the same or different, each represents a hydrogen atom, a lower alkyl group, a cycloalkyl group, a phenyl lower alkyl group, or a phenyl group; and A represents a lower alkylene group; said $R^4$ and A, said $R^5$ and A, said $R^4$ and $R^5$, or said $R^5$ and $R^6$ may form a 5-membered or 6-membered nitrogen-containing heterocyclic ring which may further contain a hetero-atom together with nitrogen atom, and the pharmacologically acceptable non-toxic salts thereof. The compounds of this invention have a strong and selective antiematic activity and an effect of stimulating the gastric motility.

6 Claims, No Drawings

PYRAZINE DERIVATIVES

DETAILED DESCRIPTION OF THE INVENTION

The present invention relates to novel pyrazine derivatives and more particularly, the invention relates to pyrazine derivatives represented by the formula III

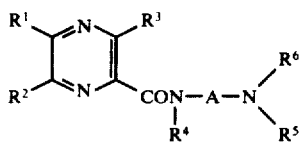

wherein $R^1$ and $R^2$, which may be the same or different, each represents a hydrogen atom, a halogen atom, a hydroxy group, a lower alkoxy group, a phenyl lower alkoxy group, a phenoxy group, a mercapto group, a lower alkylthio group, a phenyl lower alkylthio group, a phenylthio group, an amino group, a substituted amino group, a lower alkyl group, a carbamoyl group or a sulfamoyl group; $R^3$ represents a lower alkoxy group; $R^4$, $R^5$, and $R^6$, which may be the same or different, each represents a hydrogen atom, a lower alkyl group, a cycloalkyl group, a phenyl lower alkyl group, or a phenyl group; and A represents a lower alkylene group; said $R^4$ and A, said $R^5$ and A, said $R^4$ and $R^5$, or said $R^5$ and $R^6$ may form a 5-membered or 6-membered nitrogen-containing heterocyclic ring which may further contain a hetero-atom together with nitrogen atom and the pharmacologically acceptable non-toxic salt thereof.

As the compounds of this invention exhibit a strong and selective antiemetic activity and an effect of stimulating the gastric motility, these compounds are novel and useful medicaments for administration as an antiemetic agent and an agent fortreating acute or chronic gastric diseases.

In the compounds of this invention shown by formula III, $R^1$ and $R^2$ represent, typically, a hydrogen atom; a halogen atom such as a chlorine atom, a bromine atom, etc.; a hydroxy group; a lower alkoxy group such as a methoxy group, an ethoxy group, a propoxy group, a butoxy group, etc.; a phenyl lower alkoxy group such as a benzyloxy group, etc.; a phenoxy group; a mercapto group; a lower alkylthio group such as a methylthio group, an ethylthio group, a lower alkylthio group such as a benzylthio group, etc.; a phenylthio butylthio group. etc.; a phenyl group; an amino group; a substituted amino group such as a methylamino group, an ethylamino group, an isopropylamino group, a butylamino group, a dimethylamino group, a diethylamino group, a cyclohexylamino group, an allylamino group, an anilino group, a 2-hydroxyethylamino group, a 2-(diethylamino)ethylamino group, an acetylamino group, a benzylamino group, a benzoylamino group, a pyrrolidino group, a piperazine group, a morpholino group, a piperazino group, a 4-methylpiperazino group, etc.; a lower alkyl group such as a methyl group, an ethyl group, propyl group, an isopropyl group, a butyl group, etc.; a carbamoyl group; or a sulfamoyl group. Also, $R^3$ represents typically a lower alkoxy group such as a methoxy group, an ethoxy group, a propoxy group, a butoxy group, etc. $R^4$, $R^5$, and $R^6$ represent typically a hydrogen atom; a lower alkyl group such as a methyl group, an ethyl group, an isopropyl group, a butyl group, etc.; a cycloalkyl group such as a cyclopentyl group, a cyclohexyl group, etc.; a phenyl lower alkyl group such as a benzyl group, a phenethyl group, etc.; or a phenyl group. A represents typically a lower alkylene group such as a methylene group, an ethylene group, a 1,3-propylene group, a 1,4-butylene group, a 1-methylethylene group, a 2-ethylene group, etc. In the compounds of this invention shown by the general formula (III) the lower alkyl group, the phenyl lower alkyl group and the phenyl group each may be further substituted by a hydroxy group, a mercapto group, an amino group, or the like.

Furthermore, $R^4$ and A, $R^5$ and A, $R^4$ and $R^5$, or $R^5$ and $R^6$ may form a 5-membered or 6-membered nitrogen-containing heterocyclic ring which may further contain a hetero-atom such as a nitrogen atom, an oxygen atom together with the nitrogen atom and as such nitrogen-containing heterocyclic rings, there are illustrated a pyrrolidine ring, a piperidine ring, a piperazine ring, a morpholine ring, an imidazolidine ring, etc. For example, as the group shown by

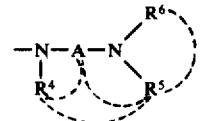

there are a 3-diethylaminopyrrolidino group, a 3-(diethylaminomethyl)pyrrolidino group, a 3-dimethylaminopiperidino group, a 4-diethylaminopiperidino group, a 3-diethylaminomorpholino group, a (1-ethylpyrrolidine-2-ylmethyl)amino group, a (1-methylpyrrolidine-2-ylmethyl)amino group, a (1-cyclohexylpyrrolidine-2-yl)amino group, a N-(1-ethylpyrrolidine-2-ylmethyl)-N-methylamino group, a (1-methylpyrrolidine-2-yl)amino group, a (1-ethylpyrrolidin-3-yl)amino group, a (1-cyclohexylpyrrolidine3-yl)amino group, a (1-ethylpiperidine-3-yl)amino group, a (1-ethylmorpholino-2-ylmethyl)amino group, a (1-ethylpiperazine-3-yl)amino group, a (1-cyclohexylpyrrolidine-2-ylmethyl)amino group, a (1-benzylpyrrolidine-2-ylmethyl)-amino group, a 4-methylpiperazino group, a 3-methylimidazolidino group, a 4-cyclohexylpiperazino group, a 4-benzylpiperazino group, a (2-pyrrolidinoethyl)amino group, a (2-piperidinoethyl)amino group, and a (2-morpholinoethyl)amino group.

In the preferred embodiments of the pyrazine derivatives of this invention, $R^1$ is an amino group or a substituted amino group; $R^2$ is a halogen atom; $R^3$ is a lower alkoxy group; $R^4$ is a hydrogen atom or a lower alkyl group; $R^5$ and $R^6$, which may be the same or different, each is a lower alkyl group, a cycloalkyl group, a phenyl lower alkyl group, or a phenyl group; A is a lower alkylene group; and $R^4$ and A, $R^5$ and A, $R^4$ and $R^5$, or $R^5$ and $R^6$ may form a 5-membered or 6-membered nitrogen-containing heterocyclic ring which may further contain a hetero-atom together with the nitrogen atom.

Typical examples of the compounds of this invention are as follows;

N-(1-ethylpyrrolidine-2-ylmethyl)-5-amino-6-chloro-3-methoxypyrazine-2-carboxamide, N-(2-diethylaminoethyl)-5-amino-6-chloro-3-methoxypyrazine-2-carboxamide, N-(1-ethylpyrrolidine-2-ylmethyl)-5-chloro-2-methoxypyrazine-3-carboxamide, N-(2-diethylaminoethyl)-5-anilino-6-chloro-3-methoxypyrazine-2-carboxamide,
N-(2-diethylaminoethyl)-6-chloro-3,5-dimethoxypyrazine-2-carboxamide,
N-(2-diethylaminoethyl)-6-chloro-5-(2-diethylaminoethylamino)-3-methoxypyrazine-2-carboxamide,
N-(2-diethylaminoethyl)-6-chloro-5-ethylamino-3-methoxypyrazine-2-carboxamide,
N-(2-diethylaminoethyl)-3-methoxypyrazine-2-carboxamide,
N-(2-diethylaminoethyl)-6-chloro-3-methoxy-5-methylaminopyrazine-2-carboxamide,
N-(2-diethylaminoethyl)-5-n-butylamino-6-chloro-3-methoxypyrazine-2-carboxamide,
N-(1-ethylpiperidine-3-yl)-5-amino-6-chloro-3-methoxypyrazine-2-carboxamide,
N-(1-ethylpyrrolidine-2-ylmethyl-6-chloro-5-ethylamino-3-methoxypyrazine-2-carboxamide,
N-(2-diethylaminoethyl)-5-amino-6-chloro-3-ethoxypyrazine-2-carboxamide,
N-(2-diethylaminoethyl)-6-chloro-5-cyclohexylamino-3-methoxypyrazine-2-carboxamide,
N-(2-diethylaminoethyl)-6-chloro-5-diethylamino-3-methoxypyrazine-2-carboxamide,
N-(2-diethylaminoethyl)-6-chloro-3-methoxy-5-(4-methylpiperazinyl)pyrazine-2-carboxamide,
N-(2-diethylaminoethyl)-6-chloro-3-methoxypyrazine-2-carboxamide,
N-(1-ethylpyrrolidine-2-ylmethyl)-5-ethylamino-3-methoxypyrazine-2-carboxamide,
N-(1-methylpyrrolidine-2-yl)-6-chloro-5-ethylamino-3-methoxypyrazine-2-carboxamide,
N-(1-ethylpyrrolidine-2-ylmethyl)-6-chloro-3-methoxy-5-methylthiopyrazine-2-carboxamide,
N-(1-ethylpyrrolidine-2-ylmethyl)-6-chloro-3,5-dimethoxypyrazine-2-carboxamide,
6-chloro-5-ethylamino-3-methoxypyrazine-2-carboxylic acid (4-methyl)piperazide,
N-(3-diethylaminopropyl)-6-chloro-5-ethylamino-3-methoxypyrazine-2-carboxamide,
N-(1-ethylpyrrolidine-2-ylmethyl)-5-benzylamino-6-chloro-3-methoxypyrazine-2-carboxamide,
N-(1-ethylpyrrolidine-2-ylmethyl)-6-chloro-3-methoxy-5-(o-methoxyphenoxy)pyrazine-2-carboxamide,
N-(1-cyclohexylpyrrolidine-2-ylmethyl)-6-chloro-5-ethylamino-3-methoxypyrazine-2-carboxamide,
N-(1-ethylpyrrolidine-2-ylmethyl)-5-amino-6-bromo-3-methoxypyrazine-2-carobxamide,
N-(1-cyclohexylpyrrolidine-3-yl)-6-chloro-5-ethylamino-3-methoxypyrazine-2-carboxamide,
N-(1-ethylpyrrolidine-2-ylmethyl)-5-allylamino-6-chloro-3-methoxypyrazine-2-carboxamide,
N-(2-piperidinoethyl)-6-chloro-5-ethylamino-3-methoxypyrazine-2-carboxamide,
N-[2-(N-benzyl-N-methylamino)ethyl]-6-chloro-5-ethylamino-3-methoxypyrazine-2-carboxamide,
N-[2-(methylamino)ethyl]-5-ethylamino-3-methoxypyrazine-2-carboxamide,
N-(2-diethylaminoethyl)-N-methyl-6-chloro-5-ethylamino-3-methoxypyrazine-2-carboxamide,
N-(2-morpholinoethyl)-6-chloro-5-ethylamino-3-methoxypyrazine-2-carboxamide,
N-[2-(N-methyl-N-phenylamino)ethyl]-6-chloro-5-ethylamino-3-methoxypyrazine-2-carboxamide,
6-chloro-5-ethylamino-3-methoxypyrazine-2-carboxylic acid (3-dimethylamino)piperizide,
N-(1-ethylpyrrolidine-2-ylmethyl)-6-benzylthio-5-ethylamino-3-methoxypyrazine-2-carboxamide,
N-(1-ethylpyrrolidine-2-ylmethyl)-3,5,6-trimethoxypyrazine-2-carboxamide,
N-(1-ethylpyrrolidine-2-ylmethyl)-N-methyl-6-chloro-5-ethylamino-3-methoxypyrazine-2-carboxamide,
N-(1-cyclohexylpyrrolidine-2-ylmethyl)-N-methyl-6-chloro-5-ethylamino-3-methoxypyrazine-2-carboxamide,
N-(1-ethylpyrrolidine-2-ylmethyl)-6-chloro-5-hydroxy-3-methoxypyrazine-2-carboxamide,
N-(1-ethylpyrrolidine-2-ylmethyl)-6-chloro-5-mercapto-3-methoxypyrazine-2-carboxamide,
N-(1-ethylpyrrolidine-2-ylmethyl)-6-chloro-3-methoxy-5-phenoxypyrazine-2-carboxamide,
N-(1-ethylpyrrolidine-2-ylmethyl)-6-chloro-3-methoxy-5-phenylthiopyrazine-2-carboxamide,
N-(1-ethylpyrrolidine-2-ylmethyl)-5-benzyloxy-6-chloro-3-methoxypyrazine-2-carboxamide,
N-(1-ethylpyrrolidine-2-ylmethyl)-5-benzylthio-6-chloro-3-methoxypyrazine-2-carboxamide,
N-(1-cyclohexylpyrrolidine-2-ylmethyl)-5-ethylamino-3-methoxypyrazine-2-carboxamide,
N-(1-phenylpyrrolidine-2-ylmethyl)-6-chloro-5-ethylamino-3-methoxypyrazine-2-carboxamide,
N-(1-benzylpyrrolidine-2-ylmethyl)-6-chloro-5-ethylamino-3-methoxypyrazine-2-carboxamide,
6-chloro-5-ethylamino-3-methoxypyrazine-2-carboxylic acid (3-diethylamino)pyrrolidide,
N-(1-ethylimidazolidine-5-ylmethyl)-6-chloro-5-ethylamino-3-methoxypyrazine-2-carboxamide,
6-chloro-5-ethylamino-3-methoxypyrazine-2-carboxylic acid (3-methyl)imidazolidide,
N-[2-(4-methylpiperazino)ethyl]-6-chloro-5-ethylamino-3-methoxypyrazine-2-carboxamide,
N-(2-pyrrolidinoethyl)-6-chloro-5-ethylamino-3-methoxypyrazine-2-carboxamide,
6-chloro-5-ethylamino-3-methoxypyrazine-2-carboxylic acid (4-cyclohexyl)piperazide,
6-chloro-5-ethylamino-3-methoxypyrazine-2-carboxylic acid (4-benzyl)piperazide,
N-(1-ethylpiperazine-3-yl)-6-chloro-5-ethylamino-3-methoxypyrazine-2-carboxamide,
6-chloro-5-ethylamino-3-methoxypyrazine-2-carboxylic acid (3-diethylaminomethyl)pyrrolidide,
6-chloro-5-ethylamino-3-methoxypyrazine-2-carboxylic acid (4-diethylamino)piperazide,
N-(1-ethylpyrrolidine-2-ylmethyl)-3-methoxy-6-sulfamoylpyrazine-2-carboxamide,
N-(1-ethylpyrrolidine-2-ylmethyl)-6-chloro-3-methoxy-5-sulfamoylpyrazine-2-carboxamide,
N-(1-ethylpyrrolidine-2-ylmethyl)-3-methoxy-5-sulfamoylpyrazine-2-carboxamide,
N-(1-ethylpyrrolidine-2-ylmethyl)-5-carbamoyl-6-chloro-3-methoxypyrazine-2-carboxamide,
N-(1-ethylpyrrolidine-2-ylmethyl)-5-chloro-6-ethylamino-3-methoxypyrazine-2-carboxamide,
N-(1-ethylpyrrolidine-2-ylmethyl)-6-ethylamino-3-methoxypyrazine-2-carboxamide,
N-(1-ethylpyrrolidine-2-ylmethyl)-6-chloro-3-methoxy-5-methylpyrazine-2-carboxamide,
N-(1-ethylpyrrolidine-2-ylmethyl)-3-methoxy-5,6-dimethylpyrazine-2-carboxamide, and
N-(2-diethylaminoethyl)-3-methoxy-5,6-dimethylpyrazine-2-carboxamide.

Among the aforesaid compounds, N-(1-ethylpyrrolidine-2-ylmethyl)-6-chloro-5-ethylamino-3-methoxypyrazine-2-carboxamide is particularly preferable.

As the pharmacologically acceptable non-toxic salts of the compounds of this invention represented by formula III, there are the acid addition salts thereof with an inorganic acid such as hydrochloric acid, hydrobromic acid, sulfuric acid, nitric acid, phosphoric acid, etc., and an organic acid such as citric acid, acetic acid, lactic acid, tartaric acid, succinic acid, fumaric acid, maleic acid, etc., and further, the quaternary ammonium salts thereof obtained by the reactions with methyl iodide, ethyl iodide, methyl bromide, benzyl bromide, dimethyl sulfate, methyl p-toluene sulfonate, methane sulfonate, etc.

As a medicament having an effect of stimulating the gastric motility and an antiemetic acitivity, N-(diethylaminoethyl)-4-amino-5-chloro-2-methoxybenzamide (general name; metoclopramide) has hitherto been known. Owing to its effect of stimulating gastric motility, metoclopramide can remove the unpleasant symptoms of digestive organs (e.g., a heavy feeling on the stomach, anorexia, belching, nausea, vomiting, etc.,) caused by gastritis, gastro atony, etc., which have been considered to be caused by the weakening of the gastric motility and further as the compounds have a stronger antiemetic activity than chlorpromazine which has widely been used as an antiemetic agent, the compounds have recently been marketed widely. However, the effects of metoclopramide produce catalepsy as a side effect. (see, Postgrad. Med. J., 49, Suppl., 4, 77–80(1973) and Med, Welt No. 36, 1567–69(1970)).

As the result of various investigations, the inventors have discovered that the compounds of this invention represented by general formula III have an effect of stimulating the gastric motility, completely free from catalepsy, and have a strong antiemetic activity as compared with metoclopramide.

That is, since the compounds of this invention have a stronger antiemetic activity than metoclopramide and show no catalepsy which is an unwanted side effect of metoclopramide, the antiemetic activity of the compounds is selective and strong. Furthermore, as the compounds of this invention have an effect of stimulating the gastric activity, they can remove the unpleasant symptoms of digestive organs (e.g., a heavy feeling on the stomach, anorexia, belching, nausea, vomiting, etc.,) caused by gastritis, gastro atony, etc. Therefore, the compounds of this invention are useful as an antiemetic agent and the medicaments for treating acute or chronic gastric diseases. Moreover, as the compounds of this invention also block a conditioned avoidance response besides an antiemetic activity (antiapomorphine activity), they are also useful as a psychotropic agent.

Now, Dutch Patent No. 7,304,557 issued recently discloses that the N-(1-substituted-3-pyrrolidinyl)benzamide or thiobenzamide represented by the formula

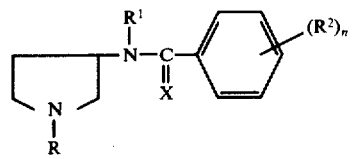

wherein R represents a cycloalkyl group, a phenyl group, or a phenylalkyl group; $R^1$ represents a hydrogen atom, a lower alkyl group, or a phenyl group; $R^2$ represents a halogen atom, a lower alkyl group, a lower alkoxy group, a nitro group, a monoalkylamino group, a dialkylamino group, a mercaptomethyl group, a sulfamoyl group, a cyano group, a hydroxy group, a benzyloxy group, or a trifluoromethyl group; X represents an oxygen atom or a sulfur atom; and $n$ represents 0-3 have an antiemetic activity showing a weak cataleptic activity i.e., having selectivity but the patent does not teach that these compounds have an effect of stimulating the gastric motility.

It is known that compounds having a benzene ring, such as metoclopramide and the aforesaid compound, have an antiemetic activity. With respect to compounds having a pyrazine ring, it is known that they have only a diuretic activity (as described in U.S. Pat. No. 3,660,400), an anti-inflammatory activity (as described in U.S. Pat. No. 3,660,403, a hypolipemic activity (as described in British Patent No. 1,268,337) or the like but it is not known that they have an antiemetic activity.

It is an unexpected fact that the compounds of this invention having a pyrazine ring have a strong antiemetic activity which has been newly discovered by the inventors.

Now, in Experiment I shown below, the antiemetic activity and toxicity of the compounds of this invention and metoclopramide were tested and their safety margins were compared.

EXPERIMENT I a). Antiemetic activity

Each of the test samples was administered to a dog by subcutaneous injection; then 0.1 mg./kg. of apomorphine was administered to a dog by subcutaneous injection after 30 minutes, and the frequency of emesis within 30 minutes after the injection was measured. (Each dog was used only once). From the frequency of emesis, the inhibition rate was calculated and from the relation between the amount of the sample used and the inhibition rate, $ED_{50}$ (μg/kg.) was determined. Drug activity was assessed by $ED_{50}$ values.

b). Acute toxicity

Each of the test samples was injected intravenously to a mouse in the tail portion at a rate of 0.1 ml./10 g./10 sec. by an up and down method. The mortality rate after one week was checked and from the relation between the amount of the sample used and the mortality rate, $LD_{50}$ (mg/kg) was determined.

The results are shown in Table I

Table I

| Sample | Antiemetic activity $ED_{50(s.c)}$ (μg/kg) | Toxicity $LD_{50}$ (mg/kg) | Safety margin $(LD_{50}/ED_{50})$ 1/1000 |
|---|---|---|---|
| chlorpromazine | 250 | 71.4 | 0.29 |
| metoclopramide | 30 | 61 | 2.03 |
| N-(1-ethylpyrrolidin-2-ylmethyl)- | 2 | 91.3 | 45.7 |

Table I-continued

| Sample | Antiemetic activity $ED_{50(s.c)}$ ($\mu$g/kg) | Toxicity $LD_{50}$ (mg/kg) | Safety margin $(LD_{50}/ED_{50})$ 1/1000 |
|---|---|---|---|
| 5-amino-6-chloro-3-methoxypyrazine-2-carboxamide | | | |
| N-(2-diethylaminoethyl)-5-amino-6-chloro-3-methoxypyrazine-2-carboxamide | 12 | 150 | 12.5 |
| N-(1-ethylpyrrolidin-2-ylmethyl)-5-chloro-2-methoxypyrazine-3-carboxamide | 20 | 170 | 8.5 |
| N-(2-diethylaminoethyl)-6-chloro-5-ethylamino-3-methoxypyrazine-2-carboxamide | 20 | 91 | 4.55 |
| N-(2-diethylaminoethyl)-6-chloro-3-methoxy-5-methylaminopyrazine-2-carboxamide | 10 | 91 | 9.1 |
| N-(1-ethylpyrrolidin-2-ylmethyl)-6-chloro-5-ethylamino-3-methoxypyrazine-2-carboxamide | 2.6 | 61.1 | 23.5 |
| N-(2-diethylaminoethyl)-5-amino-6-chloro-3-ethoxypyrazine-2-carboxamide | 12 | 72.1 | 6.01 |
| N-(1-methylpyrrolidin-2-ylmethyl)-6-chloro-5-ethylamino-3-methoxypyrazine-2-carboxamide | 3 | 45 | 15.0 |

From the results shown in the table I, it will be understood that the compounds of this invention have a stronger antiemetic activity and greatly broader safety margin than those of metoclopramide.

Then, in Experiment II shown below, the antiemetic activity and the cataleptic activity of the compounds of this invention and motoclopramide were tested and the selectivity and the activity efficiency ($ED_{50}$ p.o/$ED_{50}$ s.c) were compared between them.

EXPERIMENT II a). Antiemetic activity

1. Subcutaneous administration:
Same as Experiment (I-a).

2. Oral administration:
Each of the test samples was mixed with lactose and was filled in capsules. The capsules were orally administered to a dog, 0.1 mg./kg. of apomorphine was administered to the dog by subcutaneous injection after 90 minutes, and then the frequency of emesis was measured within 30 minutes after the apomorphine injection. (Each dog was used only once.) The drugs were evaluated by $ED_{50}$ values in the same way as described in Experiment I-a.

b). Cataleptic activity

According to the Courvoisier's method (Courvoisier, S, Durcot, R. & Jolou, L, (1957), Psychotropic drugs (Ed. Garattini, S and Ghetti, V.), p. 373, Else vier Publishing Company, Amsterdam, London, New York, Princeton), the four limbs of a rat were placed on four rubber stoppers and when the rat could maintain the same pose for 30 seconds, the rat was determined to be positive. The catalepsy was measured every 30 minutes till 240 minutes after the subcutaneous administration of the sample. The sample that produced a positive response in rat even once was determined to be positive in the cataleptic test. From the relation between the positive response and the amount of the sample, $ED_{50}$(mg/kg) was determined. The results are shown in Table II.

Table II

| Sample | Antiemetic activity $ED_{50}$(s.c) ($\mu$g/kg) | $ED_{50}$(p.o) ($\mu$g/kg) | Catalepsy $ED_{50}$ (mg/kg) | Activity efficiency |
|---|---|---|---|---|
| chlorpromazine | 250 | 2,000 | 7 | 8.0 |
| metoclopramide | 30 | 130 | 45 | 4.3 |
| N-(1-ethylpyrrolidin-2-ylmethyl)-5-amino-6-chloro-3-methoxypyrazine-2-carboxamide | 2 | 4 | —* | 2.0 |
| N-(2-diethylaminoethyl)-5-amino-6-chloro-3-methoxypyrazine-2-carboxamide | 12 | 70 | —* | 5.8 |
| N-(2-diethylaminoethyl)-6-chloro-5-ethylamino-3-methoxypyrazine-2-carboxamide | 20 | 65 | —* | 3.3 |
| N-(1-ethylpyrrolidin-2-ylmethyl)-6-chloro-5-ethylamino-3-methoxypyrazine-2-carboxamide | 2.6 | 6 | —* | 2.3 |

The symbol * means that catalepsy was not at all recognized at 100 mg/kg and the amount of sample more than 100 mg/kg is lethal dose, $ED_{50}$ could not be measured.

From the results shown in Table II, it will be understood that as the compounds of this invention had a strong antiemetic activity as compared with metoclopramide and showed no cataleptic activity, the compounds had a selective and strong antiemetic activity. Also, it will be understood that N-(1ethylpyrrolidin-2-ylmethyl)-5-amino-6-chloro-3-methoxypyrazine-2-carboxide and N-(1-ethyl)pyrrolidin-2-ylmethyl)-6-chloro-5-ethylamino-3-methoxypyrazine-2-carboxamide among the compunds of this invention showed excellent activity effeciency of 2.0 and 2.3, respectively, and thus they will show good absorption when orally administered.

The following Experiment III, the compounds of this invention were compared with metoclopramide with respect to the effect of stimulating the gastric motility.

EXPERIMENT III

After anesthetizing a dog which had fasted overnight by intravenously injecting 30 mg./kg. of pentobarbital, each of the test samples was injected intravenously and then the spontaneous motility of the stomach was recorded by means of a polygraph (RM-150, made by Nihon Koden K. K.) according to the ballon method (Jap. J. Smooth Muscle Res., 2, 15(1966)). The results are shown in Table III. In addition, the effect of stimulating the gastric motility was denoted as (+) and (++) respectively when 10mg./kg. and 5 mg./kg. each of the sample was intervenously injected and the stimulated motility of the stomach continued longer than 20 minutes.

Table III

| Sample | Effect of stimulating gastric motility |
| --- | --- |
| Metoclopramide | ++ |
| N-(2-diethylaminoethyl)-5-anilino-6-chloro-3-methoxy-pyrazine-2-carboxamide | + to ++ |
| N-(2-diethylaminoethyl)-6-chloro-5-ethylamino-3-methoxy-pyrazine-2-carboxamide | + to ++ |
| N-(1-ethylpyrrolidin-2-ylmethyl)-6-chloro-5-ethylamino-3-methoxy-pyrazine-2-carboxamide | ++ |
| N-(1-ethylpyrrolidine-2-ylmethyl)-5-ethylamino-3-methoxy-pyrazine-2-carboxamide | ++ |

From the results shown in Table III it will be understood that the compounds of this invention had an effect of stimulating the gastric motility as metoclopramide.

The compounds of this invention shown by formula III can be prepared by reacting a pyrazinecarboxylic acid represented by formula I

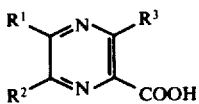

I wherein $R^1$, $R^2$, and $R^3$ have the same meaning as in formula III or the reactive derivative thereof and an amine derivative represented by formula II

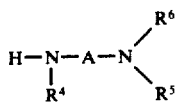

II wherein $R^4$, $R^5$, $R^6$, and A have the same meaning as in formula III.

As the reactive derivatives of the pyrazinecarboxylic acid shown by formula I, there are illustrated an acid halide and acid chloride, acid bromide, etc.; an acid azide; an ester such as a methyl ester, ethyl ester, p-nitrophenyl ester, p-chlorophenyl ester, etc.; a symmetric acid anhydride, a mixed acid anhydride such as an alkyl carbonate mixed acid anhydride prepared by reacting an alkyl halo carbonate (e.g., methyl chloro carbonate, ethyl chloro carbonate, and ethyl bromo carbonate) and the pyrazinecarboxylic acid of formula I and a mixed acid anhydride prepared by reacting an acid (e.g., alkylphosphoric acid, alkylphosphorous acid, and sulfuric acid) or the reactive derivative thereof and the pyrazinecarboxylic acid of formula I; and an active amide such as an acid imidazolide or an acid pyrrolidide prepared by reacting N,N'-carbonyldiimidazole, N,N'-thionyldiimidazole or N,N'-carbonyldipyrrole and the pyrazinecarboxylic acid of formula I and an acid 2,4-dimethylpyrazolide prepared by reacting an acid hydrazide of the pyrazinecarboxylic acid of formula I and acetylacetone.

At the practice of the production of the compounds of this invention, the pyrazinecarboxylic acid of formula I or the reactive derivative thereof may be caused to react with an equimolar amount or a slightly excessive molar amount of the amine derivative of formula II.

When the pyrazinecarboxylic acid shown by formula I is a free carboxylic acid, the pyrazinecarboxylic acid of formula I can be caused to react with the amine derivative of formula II at room temperature or under heating in an inert solvent in the presence of a condensing agent such as N,N'-dicyclohexylcarbodiimide, titanium tetrahchloride, etc. Furthermore, the amine derivative of formula II may be preliminarily reacted with a phosphorus halide such as phosphorus trichloride, phosphorus oxychloride, diethylchlorophosphite, ophenylenechlorophosphite, ethyldichlorophosphite, etc., in an inert solvent and then reacted with the pyrazinecarboxylic acid of formula I. For example, when group $R^4$ of the amine derivative of formula II is a hydrogen atom and the phosphorus halide is phosphorus trichloride, the amine derivative is first reacted with about ⅓ mol of phosphorus trichloride in an inert solvent in the presence of a tertiary base such as triethylamine, pyridine, N,N-dimethylaniline, etc., under cooling or at room temperature and then is reacted with the pyrazinecarboxylic acid of formula I at room temperature or under heating, preferably under refluxing in an inert solvent.

When an acid halide is used as the reactive derivative of the pyrazinecarboxylic acid of formula I, the reaction is usually carried out in water under cooling or at room temperature in the presence of an alkali such as sodium hydroxide, potassium hydroxide, etc., Alternatively, the reaction is usually carried out in an inert solvent under cooling or at room temperature in the presence of a tertiary base such as triethylamine, pyridine, N,N-dimethylaniline, etc. When an acid azide is used as the reactive derivative of the pyrazinecarboxylic acid of formula I, the reaction is usually carried out in water under cooling or at room temperature in the presence of an alkali such as sodium hydroxide, potassium hydroxide, etc. When an ester is used as the reactive derivative of the pyrazinecarboxylic acid of formula I, the reaction is usually carried out in an inert solvent at room temperature or under heating, preferably under refluxing. Furthermore, when a symmeteric acid anhydride or a mixed acid anhydride is used as the reactive derivative of the pyrazinecarboxylic acid of formula I, the reaction is usually carried out in an inert solvent at room temperature or under heating in the presence of, as the case may be, a tertiary base such as triethylamine, pyridine, N,N-dimethylaniline, etc. Still further, when an active amide is used as the reactive derivative of the pyrazinecarboxylic acid of formula I; the reaction is usually carried out in an inert solvent at room temperature or under heating. In addition, the reactive derivative of the pyrazinecarboxylic acid of formula I may be caused to react with the amine derivative of formula II without being isolated from the reaction mixture thereof.

The inert solvent used in the reaction of this invention is an inert organic solvent which does not participate in the reaction and preferred examples of such solvents are benzene, toluene, methanol, ethanol, isopropyl alcohol, xylene, dioxane, tetrahydrofuran, chloroform, dichloromethane etc., which may be properly selected according to the nature of the reactive derivative used.

The compounds of this invention shown by formula III thus prepared are isolated or purified by ordinary chemical operations such as extraction, recrystallization, column chromatography, and the like.

In addition, the compounds of this invention shown by formula III in which $R^1$ and/or $R^2$ is a halogen atom may be converted into the compounds of formula III in which $R^1$ and/or $R^2$ is a hydrogen atom, by catalytic reduction. In this case, if the compound has a group which may be reduced, the group is simultaneously reduced. For example, N-[2-(N-benzyl-N-methylamino)ethyl]-6-chloro-5-ethylamino-3-methoxypyrazine-2-carboxamide can be converted into N-[2-(methylamino)ethyl]-5-ethylamino-3-methoxypyrazine-2-carboxamide by subjecting the compound to a catalytic reduction in the presence of a catalyst such as palladium carbon, etc.

Furthermore, the compounds of this invention, such as, for example, N-[1-ethylpyrrolidin-2-ylmethyl]-6-chloro-5-ethylamino-3-methoxypyrazine-2-carboxamide can be converted into N-[1-ethylpyrrolidine-2-ylmethyl]-6-benzylthio-5-ethylamino-3-methoxypyrazine-2-carboxamide by a reaction with benzylmercaptan.

The compounds of this invention shown by formula III may be administered orally as, for example, tablet, powder, capsule, and syrup or parenterally by, for example, intravenous injection intramuscular injection. The dosage of the compounds of this invention is about 1-300 mg./day, preferably about 5-50 mg./day.

Now, the production of the compounds of this invention and also the starting materials for producing the compounds of this invention will be illustrated in the following examples and the reference examples.

Reference example 1: Production of methyl 5,6-dichloro-3-methoxypyrazine-2-carboxylate;

In 12 ml. of dimethylformamide was dissolved 2.0 g. of methyl 3-methoxy-pyrazine-2-carboxylate and chlorine gas was introduced in the solution while maintaining the solution at 50°-60° C. In this case, after the exothermic reaction was over, the chlorine gas was further passed through the reaction mixture for 6 hours while heating it to 70°-80° C. to complete the reaction.

After cooling, the reaction mixture was dispersed in 50 ml. of ice water and the crystals precipitated were recovered by filtration, washed with ice water, and dried to give 2,4 g (yield 85.0%) of methyl 5,6-dichloro-3-methoxypyrazine-2-carboxylate.

Reference example 2: Production of methyl 5-amino-6-chloro-3-methoxypyrazine-2-carboxylate:

In 12 ml. of dimethyl sulfoxide was dissolved 2.4 g. of methyl 5,6-dichloro-3-methoxypyrazine-2-carboxylate and ammonia gas was introduced in the solution while maintaining the solution at 65°-70° C. Then, after further passing the ammonia gas for 1.5 hours while cooling the reaction system to 10° C., the reaction mixture was dispersed in 50 ml. of chilled water and the crystals precipitated were recovered by filtration, washed with ice water, and dried to provide 1.9 g. (yield 86.4%) of methyl 5-amino-6-chloro-3-methoxypyrazine-2-carboxylate having a melting point of 158°-159° C.

Elemental analysis for $C_7H_8N_3O_3Cl$:

| | C(%) | H(%) | N(%) | Cl(%) |
|---|---|---|---|---|
| Calculated: | 38.64 | 3.71 | 19.31 | 16.29 |
| Found: | 38.85 | 3.77 | 19.23 | 16.21 |

Reference example 3: Production of methyl 5-anilino-6-chloro-3-methoxypyrazine-2-carboxylate:

In 20 ml. of isopropyl alcohol were dissolved 2.4 g. of methyl 5,6-dichloro-3-methoxypyrazine-2-carboxylate and 2.0 g. of aniline and after refluxing the solution for 5 hours, the reaction mixture was dispersed in 100 ml. of ice water. The crystals precipitated were recovered by filtration, washed with water, and dried to provide 2.5 g. of methyl 5-anilino-6-chloro-3-methoxypyrazine-2-carboxylate having a melting point of 167° C.

Elemental analysis for $C_{13}H_{12}N_3O_3Cl$:

| | C(%) | H(%) | N(%) | Cl(%) |
|---|---|---|---|---|
| Calculated: | 53.16 | 4.12 | 14.31 | 12.07 |
| Found: | 53.35 | 4.33 | 14.17 | 11.97 |

EXAMPLE 1

In 10 ml. of toluene were dissolved 2.0 g. of methyl 5-amino-6-chloro-3-methoxypyrazine-2-carboxylate and 2.0 g. of 2-amino-methyl-1-ethylpyrrolidine and then the solution was refluxed for 17 hours. After cooling, the reaction mixture was extracted with dilute hydrochloric acid. The extract was washed with chloroform, and basified with an aqueous sodium hydroxide solution, whereby an oily material was formed. The oily material was extracted with chloroform and, the extract was washed with water, dried over anhydrous magnesium sulfate and the solvent was distilled thereby forming crystals. When the crystals were recrystallized from 10 ml. of toluene, 1.2 g. of the flaky crystals of N-(1-ethylpyrrolidine-2-ylmethyl)-5-amino-6-chloro-3-methoxypyrazine-2-carboxamide having a melting point of 155° C were obtained.

Elemental analysis for $C_{13}H_{20}N_5O_2Cl$:

| | C(%) | H(%) | N(%) | Cl(%) |
|---|---|---|---|---|
| Calculated: | 49.76 | 6.42 | 22.32 | 11.30 |
| Found: | 50.01 | 6.56 | 22.08 | 11.39 |

EXAMPLE 2

To 5 ml. of toluene were added 1.5 g. of methyl 5-amino-6-chloro-3-methoxypyrazine-2-carboxylate and 1.5 g. of N,N-diethylethylenediamine and the mixture was refluxed for 5 hours. After cooling, the reaction mixture was extracted with dilute hydrochloric acid and, the extract was washed with chloroform, and then basified with an aqueous sodium hydroxide solution, whereby an oily material was formed. The oily material was extracted with chloroform and the extract was washed with water and dried over anhydrous magnesium sulfate. When the solvent was distilled off from the extract, crystals were obtained, which were recrystallized from 7 ml. of toluene to provide 1.16 g. (yield 55.8%) of the flaky crystals of N-(2-diethylaminoethyl)-5-amino-6-chloro-3-methoxypyrazine-2-carboxamide having a melting point of 158° C.

| Elemental analysis for $C_{12}H_{20}N_5O_2Cl$ | | | |
|---|---|---|---|
| | C(%) | H(%) | N(%) | Cl(%) |
| Calculated: | 47.76 | 6.68 | 23.21 | 11.75 |
| Found: | 48.04 | 6.73 | 22.93 | 11.99 |

EXAMPLE 3

A mixture of 2.0 g. of methyl 5-chloro-2-methoxypyrazine-3-carboxylate, 2.0 g. of 2-aminomethyl-1-ethylpyrrolidine and 20 ml. of methanol was refluxed for one hour. The solvent was distilled off and the residue was dissolved in dilute hydrochloric acid. The solution was washed with chloroform and basified with an aqueous sodium hydroxide solution, whereby an oily material was formed. The oily material was extracted with chloroform, and the extract was washed with water and dried and, the solvent was distilled off to provide 1.7 g. of an oily material, which was dissolved in absolute ethanol. After introducing dry hydrogen chloride gas into the solution, ethanol was distilled off and the residue was recrystallized from acetone to provide 1.7 g. of N-(1-ethylpyrrolidine-2-ylmethyl)-5-chloro-2-methoxypyrazine-3-carboxamide hydrochloride having a melting point of 188° C.

| Elemental analysis for $C_{13}H_{20}N_4O_2Cl_2$: | | | |
|---|---|---|---|
| | C(%) | H(%) | N(%) | Cl(%) |
| Calculated: | 46.58 | 6.01 | 16.71 | 21.15 |
| Found: | 46.75 | 6.04 | 16.47 | 20.89 |

EXAMPLE 4

In 20 ml. of methanol were dissolved 2.0 g. of methyl 5-anilino-6-chloro-3-methoxypyrazine-2-carboxylate and 2.0 g. of N,N-diethylethylenediamine and the solution was refluxed for 24 hours. Then, methanol was distilled off and the residue was dissolved in dilute hydrochloric acid. The solution was washed with chloroform and then basified with an aqueous sodium hydroxide solution, whereby crystals were precipitated. The crystals were extracted with chloroform, after washing with water and drying the extract, the solvent was distilled off from the extract, and the crystals obtained were recrystallized from toluene to provide 1.8 g. of N-(2-diethylaminoethyl)-5-anilino-6-chloro-3-methoxypyrazine-2-carboxamide having a melting point of 159°-161° C.

| Elemental analysis for $C_{18}H_{24}N_5O_2Cl$: | | | |
|---|---|---|---|
| | C(%) | H(%) | N(%) | Cl(%) |
| Calculated: | 57.21 | 6.40 | 18.53 | 9.38 |
| Found: | 57.43 | 6.28 | 18.25 | 9.47 |

EXAMPLE 5

A mixture of 1.3 g. of methyl 6-chloro-3,5-dimethoxypyrazine-2-carboxylate, 1.3 g. of N,N-diethylethylene diamine, and 10 ml. of toluene was refluxed for 3.5 hours. After cooling, the reaction mixture was extracted with dilute hydrochloric acid and the extract was washed with chloroform and basefield with an aqueous sodium hydroxide solution, whereby an oily material was formed. The oily material was extracted with chloroform and the extract was washed with water, dried and then the solvent was distilled off to provide an oily residue. A small amount of n-hexane was added to the residue and crystals formed were recovered by filtration and recrystallized from n-hexane to provide 0.8 g. of methyl 6-chloro-5-(2-diethylamonioethylamino)-3-methoxypyrazine-2-carboxylate having a melting point of 105°-106° C.

The n-hexane mother liquor was evaporated under reduced pressure to dryness and the oily residue was triturated with a small amount of peterolium ether, whereby crystals were formed. When the crystals were recrystallized from n-hexane, 0.2 g. of N-(2-diethylaminoethyl)-6-chloro-3,5-dimethoxypyrazine-2-carboxamide having a melting point of 88° C was obtained.

In addition, when a mixture of the methyl 6-chloro-5-(2-diethylaminoethylamino)-3-methoxypyrazine-2-carboxylate obtained above and N,N-diethylethylenediamine were heated in toluene, N-(2-diethylaminoethyl)-6-chloro-5-(2-diethylaminoethylamino)-3-methoxypyrazine-2-carboxamide having a melting point of 112° C was obtained.

Reference example 4: Production of methyl 6-chloro-5-ethylamino-3-methoxypyrazine-2-carboxylate:

To 24 ml. of isopropyl alcohol were added 2.4 g. of methyl 5,6-dichloro-2-methoxypyrazine-2-carboxylate, 1.1 g. of ethylamine hydrochloride, and 2.2 g. of triethylamine and the mixture was refluxed for one hour. After the reaction was over, the solvent was distilled off from the reaction mixture and the solid residue obtained was washed with 100 ml. of water to provide 2.26 g. of the yellow crystals of methyl 6-chloro-5-ethylamino-3-methoxypyrazine-2-carboxylate. When the crystals were recrystallized from benzene, yellow prism crystals were obtained having a melting point of 128° C.

| Elemental analysis for $C_9H_{12}N_3O_3Cl$; | | |
|---|---|---|
| | C(%) | H(%) | N(%) |
| Calculated: | 44.00 | 4.92 | 17.10 |
| Found: | 44.08 | 4.91 | 16.90 |

Reference example 5: Production of methyl 6-chloro-3-methoxy-5-methylaminopyrazine-2-carboxylate:

To 24 ml. of isopropyl alcohol were added 2.4 g. of methyl 5,6-dichloro-3-methoxypyrazine-2-carboxylate, 0.8 g. of methylamine hydrochloride and 2.2 g of triethylamine and the mixture was refluxed for one hour. After the reaction was over, the solvent was distilled off under reduced pressure from the reaction mixture and when 50 ml. of water was added to the residue obtained, a suspension was obtained. The suspension was extracted three times each time with 50 ml. of chloroform. The extracts were combined and washed with water, dried, and the solvent was distilled off under reduced pressure to provide 2.0 g. of light yellow crystals of methyl 6-chloro-3-methoxy-5-methylaminopyrazine-2-carboxylate. The light yellow acicular crystals obtained by recrystallizing the product from benzene, melted at 147° C.

Mass spectra (m/e): 233 (M+), 231 (M+),

Reference example 6: Production melted point methyl 5-n-butylamino-6-chloro-3-methoxypyrazine-2-carboxylate;

To 24 ml. of isopropyl alcohol were added 2.4 g. of methyl 5,6-dichloro-3-methoxypyrazine-2-carboxylate, 0.8 g. of n-butylamine, and 1.1 g. of triethylamine and the mixture was refluxed for one hour. After reaction was over, the solvent was distilled off under reduced pressure from the reaction mixture and the residue obtained was washed with 50 ml of water and dried to provide 2.56 g. of light yellow crystals of methyl 5-n-butylamino-6-chloro-3-methoxypyrazine-2-carboxylate. The light yellow acicular crystals obtained by recrystallizing the product from n-hexane melted at 92° C.

| Elemental analysis for $C_{11}H_{16}N_3O_3Cl$: | | |
|---|---|---|
| C(%) | H(%) | N(%) |
| Calculated: 48.27 | 5.89 | 15.35 |
| Found: 48.35 | 5.97 | 15.12 |

Reference example 7: Production of ethyl 5-amino-6-chloro-3-ethoxypyrazine-2-carboxylate:

a. While refluxing a solution of sodium ethylate prepared from 0.3 g. of metallic sodium and 20 ml. of ethanol, a solution containing 4.1 g. of methyl 3-chloropyrazine-2-carboxylate in 20 ml. of ethanol was added dropwise to the solution over a period of 10 minutes and then the mixture was refluxed for 90 minutes. After cooling, the solvent was distilled off under reduced pressure from the reaction mixture, the residue obtained was mixed well with 50 ml. of water by shaking well, and then the mixture was extracted three times each time with 30 ml. of dichloromethane. The extracts were combined, washed with water, dried, and then the solvent was distilled off under reduced pressure to provide 3.5 g. of a light yellow oily material of ethyl 3-ethoxypyrazine-2-carboxylate.

Mass spectra (m/e): 196(M+)

b. While maintaining at 10°-30° C. the solution obtained by dissolving 3.5 g. of ethyl 3-ethoxypyrazine-2-carboxylate in 20 ml. of dimethylformamide, chlorine gas was passed through the solution for 1 hour and then while maintaining the solution at 70°-75° C., chlorine gas was further passed through the solution for 3 hours. After cooling, the reaction mixture was dispersed in 200 ml. of ice water and the colorless crystals thus formed were recovered by filtration, washed with water and dried. The crystals were then extracted with 200 ml. of hot n-hexane. By distilling off the solvent from the extract under reduced pressure, 4.6 g. of ethyl 5,6-dichloro-3-ethoxypyrazine-2-carboxylate was obtained. The colorless acicular crystals obtained by recrystallizing the product from n-hexane melted at 56°-57° C.

| Elemental analysis for $C_9H_{10}N_2O_3Cl_2$: | | |
|---|---|---|
| C(%) | H(%) | N(%) |
| Calculated: 40.78 | 3.80 | 10.57 |
| Found: 40.60 | 3.69 | 10.66 | c. While maintaining at 65°-70° C. the solution obtained by dissolving 2.0 g. of ethyl 5,6-dichloro-3-ethoxypyrazine-2-carboxylate in 20 ml. of dimethylsulfoxide, ammonia gas was passed through the solution for 40 minutes. Then after allowing to stand the reaction mixture for one hour at room temperature, it was dispersed in 300 ml. of ice water and the yellow acicular crystals formed were recovered by filtration to provide 1.5 g. of ethyl 5-amino-6-chloro-3-ethoxypyrazine-2-carboxylate. The light yellow acicular crystals obtained by recrystallizing the product from a mixture of benzene and n-hexane melted at 110°-111° C.

| Elemental analysis for $C_9H_{12}N_3O_3Cl$: | | |
|---|---|---|
| C(%) | H(%) | N(%) |
| Calculated: 44.00 | 4.92 | 17.10 |
| Found: 44.09 | 4.98 | 16.99 |

EXAMPLE 6

In 14 ml. of isopropyl alcohol were dissolved 1.4 g. of methyl 6-chloro-5-ethylamino-3-methoxypyrazine-2-carboxylate and 1.4 g. of N,N-diethylethylenediamine and the solution was refluxed for 4 days. After the reaction was over, the solvent was distilled off under reduced pressure from the reaction mixture and the residue obtained was applied to a silica gel column chromatography. The column was then developed using a mixture of ether and N-hexane of 1:1 volume ratio as an eluting solution. From the 1st fraction 0.7 g. of methyl 5-ethylamino-6-chloro-3-methoxypyrazine-2-carboxylate used as the starting material was recovered and from the 2nd fraction 0.7 g. of colorless plate crystals of N-(2-diethylaminoethyl)-6-chloro-5-ethylamino-3-methoxypyrazine-2-carboxamide a melting at 142° C. were obtained. The product obtained by recrystallizing the crystals from a mixture of benzene and n-hexane melted at 142° C.

| Elemental analysis for $C_{14}H_{24}N_5O_2Cl$: | | |
|---|---|---|
| C(%) | H(%) | N(%) |
| Calculated: 50.98 | 7.33 | 21.23 |
| Found: 51.06 | 7.47 | 20.96 |

EXAMPLE 7

In 5 ml. of ethanol were dissolved 1.3 g. of methyl 3-methoxypyrazine-2-carboxylate and 1.3 g. of N,N-diethylethylenediamine and the solution was refluxed for 4 hours. The solution was then allowed to stand overnight at room temperature. After the reaction was over, ethanol was distilled off under reduced pressure from the reaction mixture and the residue formed was dissolved in 5 ml. of chloroform and the solution was washed twice each time with 5 ml. of water. Then, after acidifying the solution with hydrochloric acid, the solution was extracted three times each time with 5 ml. of water. The extracts were combined and after basfying the extract with aqueous ammonia, extracted three times each with 5 ml. of chloroform. The extracts were combined, washed with water, dried, and then chloroform was distilled off under reduced pressure to provide 1.6 g. of light-yellow oily N-(2-diethylaminoethyl)-3-methoxypyrazine-2-carboxamide.

Mass spectra (m/e): 252(M+).

EXAMPLE 8

In 35 ml. of isopropyl alcohol were dissolved 3.5 g. of methyl 6-chloro-3-methoxy-5-methylaminopyrazine-2-carboxylate and 3.5 g. of N,N-diethylethylenediamine and the solution was refluxed for one day. After the reaction was over, the solvent was distilled off under a reduced pressure from the reaction mixture and the residue formed was dissolved in 50 ml. of chloroform. After washing the solution twice each time with 30 ml. of water, the solution was acidified with hydrochloric acid and extracted three times each time with 20 ml. of water. (The chloroform layer was washed with water, dried, and evaporated to dryness, whereby 2.4 g of methyl 6-chloro-3-methoxy-5-methylaminopyrazine-2-carboxylate used as the starting material was recovered.). The aqueous extracts were combined, neutralized with diluted aqueous ammonia, and then extracted three times each time with 30 ml. of chloroform. The extracts were combined, washed with water, dried, and then chloroform was distilled off under reduced pressure to provide 1.4 g. of N-(2-diethylaminoethyl)-6-chloro-3-methoxy-5-methylaminopyrazine-2-carboxamide. The colorless plate crystals obtained by recrystallizing the product from benzene melted at 157° C.

Elemental analysis for $C_{13}H_{22}N_5O_2Cl$:

|  | C(%) | H(%) | N(%) |
|---|---|---|---|
| Calculated: | 49.44 | 7.02 | 22.18 |
| Found: | 49.50 | 7.09 | 21.95 |

EXAMPLE 9

In 30 ml. of isopropyl alcohol were dissolved 3.0 g. of methyl 5-n-butylamino-6-chloro-3-methoxypyrazine-2-carboxylate and 2.5 g. of N,N-diethylethylenediamine and the solution was refluxed for one day. After the reaction was over, the solvent was distilled off under reduced pressure from he reaction mixture and the residue was dissolved in 50 ml. of chloroform. Afther washing the solution twice each with 30 ml. of water, the solution was acidified with hdyrochloric acid and extracted three times each time with 20 ml. of water. (The chloroform layer was washed with water, dried, and the evaporated to dryness, whereby 0.9 g. of methyl 5-n-butylamino-6-chloro-3-methoxypyrazine-2-carboxylate used as the starting material was recovered.). The aqueous extracts were combined, nuetralized with dilute aqueous ammonia, and then extracted three times, each time with 30 ml. of chloroform. The extracts were combined, washed with water, dried, and then chlorogorm was distilled off under reduced pressure to provide 1.0 g. of N-(2-diethylaminoethyl)-5-n-butylamino6-chloro-3-methoxypyrazine-2-carboxamide. The colorless plate crystals obtained by recrystallizing the product from a mixture of benzene and n-hexane melted at 127° C.

Elemental analysis for $C_{16}H_{28}N_5O_2Cl$:

|  | C(%) | H(%) | N(%) |
|---|---|---|---|
| Calculated: | 53.70 | 7.89 | 19.57 |
| Found: | 53.67 | 8.00 | 19.44 |

EXAMPLE 10

In 5 ml. of toluene were dissolved 500 mg. of methyl 5-amino-6-chloro-3-methoxypyrazine-2-carboxylate and 500 mg. of 3-amino-1-ethylpiperidine and the solution was refluxed for 30 hours. After cooling, the reaction mixture was extracted three times each time with 5 ml. of dilute hydrochloric acid and the combined extract was washed three times each time with 5 ml. of chloroform. (The organic layer was combined with the chloroform and the mixture was washed with water, dried, and then the solvent was distilled off under reduced pressure, whereby 300 mg. of methyl 5-amino-6-chloro-3-methoxypyrazine-2-carboxylate used as the starting material was recovered.). The extract was basified with a 3 N aqueous sodium hydroxide solution and the oily material formed was extracted twice each time with 10 ml. of chloroform. The extracts were combined, washed with water, dried, and chloroform was distilled off under reduced pressure to provide an oily residue. The residue was triturated with a small amount of petroleum ether, whereby crystals were formed. The crystals were recovered by filtration and recrystallized from toluene to provide 90 mg. of N-(1-ethylpiperidin -3-yl)-5-amino-6-chloro-3-methoxypyrazine-2-carboxamide melting at 168°-169° C.

Elemental analysis for $C_{13}H_{20}N_5O_2Cl$:

|  | C(%) | H(%) | N(%) | Cl(%) |
|---|---|---|---|---|
| Calculated: | 49.76 | 6.42 | 22.32 | 11.30 |
| Found: | 49.95 | 6.48 | 22.10 | 11.38 |

EXAMPLE 11

In 20 ml. of methanol were dissolved 2.0 g. of methyl 6-chloro-5-ethylamino-3-methoxypyrazine-2-carboxylate and 2.0 g. of 2-aminomethyl-1-ethylpyrrolidine and the solution was refluxed for 24 hours. After cooling, the solvent was distilled off under reduced pressure from the reaction mixture to provide an oily residue. The residue was dissolved in 30 ml. of a dilute aqueous hydrochloric acid solution and the solution was washed three times each time with 10 ml. of chloroform. (The chloroform washings was washed with water, dried, and then the solvent was distilled off under reduced pressure, whereby 1.05 g. of methyl 6-chloro-5-ethylamino-3-methoxypyrazine-2-carboxylate used as the starting material was recovered.). The aqueous layer was basified with a 3 N aqueous sodium hydroxide solution and the oily material formed was extracted with 30 ml. of chloroform. The extract was washed with water, dried, the solvent was distilled off under reduced pressure, and the oily residue formed was allowed to stand, whereby the oily residue was crystallized. After recrystallizing the crystals from toluene, 0.88 g. of N-(1-ethylpyrrolidin-2-ylmethyl)-6-chloro-5-ethylamino-3-methoxypyrazine-2-carboxamide melting at 167°-169° C was obtained.

Elemental analysis for $C_{15}H_{24}N_5O_2Cl$:

|  | C(%) | H(%) | N(%) | Cl(%) |
|---|---|---|---|---|
| Calculated: | 52.70 | 7.08 | 20.49 | 10.37 |
| Found: | 52.82 | 7.20 | 20.43 | 10.57 |

EXAMPLE 12

To 8 ml. of toluene were added 0.8 g. of ethyl 5-amino-6-chloro-3-ethoxypyrazine-2-carboxylate and 0.8 g. of N,N-diethylethylenediamine and the mixture was refluxed for 20 hours. After the reaction was over, the reaction mixture was cooled to room temperature and then extracted with 20 ml. of a 1 N aqueous hydrochloric acid solution. The extract was neutralized with dilute aqueous ammonia under ice-cooling and then extracted three times each time with 30 ml. of chloroform. The extracts were combined washed with water dried, and then the solvent was distilled off under reduced pressure. By washing the residue obtained with 30 ml. of n-hexane, 0.53 g. of colorless crystals of N-(2-diethylaminoethyl)-5-amino-6-chloro-3-ethoxypyrazine-2-carboxamide was obtained. The colorless acicular crystals obtained by recrystallizing the product from a mixture of benzene and n-hexane melted at 147°-148° C.

Elemental analysis for $C_{13}H_{22}N_5O_2Cl$:

|  | C(%) | H(%) | N(%) |
|---|---|---|---|
| Calculated: | 49.44 | 7.02 | 22.18 |
| Found: | 49.42 | 6.83 | 21.79 |

Reference example 8: Production of methyl 6-chloro-5-cyclohexylamino-3-methoxypyrazine-2-carboxylate:

To 24 ml. of isopropyl alcohol were added 2.4 g. of methyl 5,6-dichloro-3-methoxypyrazine-2-carboxylate, 1.1 g. of cyclohexylamine and 1.1g of triethylene and the mixture was refluxed for one hour. After the reaction was over, the solvent was distilled off under reduced pressure from the reaction mixture and the residue obtained was washed with 100 ml. of water and dried to 2.5 g. of colorless crystals of methyl 6-chloro-5-cyclohexylamino-3-methoxypyrazine-2-carboxylate.
The colorless prism crystals obtained by recrystallizing the product, melted at 100° C.

| Elemental analysis for $C_{13}H_{18}N_3O_3Cl$: | | | |
|---|---|---|---|
| | C(%) | H(%) | N(%) |
| Calculated: | 52.09 | 6.05 | 14.02 |
| Found: | 52.27 | 6.19 | 13.65 |

Reference example 9. Production of methyl 6-chloro-5-diethylamino-3-methoxypyrazine-2-carboxylate:

To 24 ml. of isopropyl alcohol were added 2.4 g. of methyl 5,6-dichloro-3-methoxypyrazine-2carboxylate, 0.8 g. of diethylamine, and 1.1 g. of triethylamine and the mixture was refluxed for one hour. After the reaction was over, the solvent was distilled off under reduced pressure from the reaction mixture and the oily residue obtained was allowed to stand overnight, whereby the oily residue was crystallized. The crystals were washed twice each time with 50 ml. of water, and dried to provide 2.4 g. of pink crystals of methyl 6-chloro-5-diethylamino-3-methoxypyrazine-2-carboxylate. The colorless prism crystals obtained by recrystallizing the product from n-hexane melted at 60° C.

| Elemental analysis for $C_{11}H_{16}N_3O_3Cl$: | | | |
|---|---|---|---|
| | C(%) | H(%) | N(%) |
| Calculated: | 48.27 | 5.89 | 15.35 |
| Found: | 48.29 | 5.90 | 15.32 |

Reference example 10: Production of methyl 6-chloro-3-methoxy-5-(4-methylpiperazinyl)pyrazine-2-carboxylate:

To 10 ml. of isopropyl alcohol were added 364 mg. of methyl 5,6-dichloro-3-methoxypyrazine-2-carboxylate and 342 mg. of 1-methylpiperazine and the mixture was refluxed for one hour. After the reaction was over, the solvent was distilled off under reduced pressure from the reaction mixture and the residue obtained was added to 30 ml. of water, mixed well and, the mixture was extracted twice each time with 30 ml. of chloroform. The extracts were combined, washed with water, dried, and the solvent was distilled off under reduced pressure to provide 420 mg. of light yellow crystals of methyl 6-chloro-3-methoxy-5-(4-methylpiperazinyl)-pyrazine-2-carboxylate. The colorless acicular crystals obtained by recrystallizing the product from a mixture of benzene and n-hexane melted at 110° C.

| Elemental analysis for $C_{12}H_{17}N_4O_3Cl$: | | | |
|---|---|---|---|
| | C(%) | H(%) | N(%) |
| Calculated: | 47.92 | 5.70 | 18.63 |
| Found: | 48.04 | 5.78 | 18.39 |

EXAMPLE 13

In 24 ml. of isopropyl alcohol were dissolved 2.4 g. of methyl 6-chloro-5-cyclohexylamino-3-methoxypyrazine-2-carboxylate and 2.0 g. of N,N-diethylethylenediamine and the solution was refluxed for 2 days. After the reaction was over, the solvent was distilled off under reduced pressure from the reaction mixture and then 50 ml. of ether was added to the oily residue obtained, whereby crystals were formed. The crystals were recovered by filtration and washed twice each time with 50 ml. of ether to provide 2.5 g. of colorless prism crystals of N-(2-diethylaminoethyl)-6-chloro-5-cyclohexylamino-3-methoxypyrazine-2-carboxamide. The crystals obtained by recrystallizing the product from toluene melted at 140° C.

| Elemental analysis for $C_{18}H_{30}N_5O_2Cl$: | | | |
|---|---|---|---|
| | C(%) | H(%) | N(%) |
| Calculated: | 56.31 | 7.88 | 18.24 |
| Found: | 56.33 | 7.94 | 18.04 |

EXAMPLE 14

In 30 ml. of isopropyl alcohol were dissolved 3.0 g. melted at methyl 6-chloro-5-diethylamino-3-methoxypyrazine-2-carboxylate and 2.5 g. of N,N-diethylethylenediamine and the solution was refluxed for 3 days. After the reaction was over, the solvent was distilled off under reduced pressure from the reaction mixture and the residue obtained was dissolved in 50 ml. of chloroform. The solution was washed twice each time with 30 ml. of water, acidified with hydrochloric acid, and was extracted three times each time with 20 ml. of water. The extracts were combined and after neutralizing with dilute aqueous ammonia, extracted three times each time with 30 ml. of chloroform. The extracts were combined, washed with water, dried, and then chloroform and distilled off under reduced pressure to provide 2.3 g. of crude oily N-(2-diethylaminoethyl)-6-chloro-5-diethylamino-3-methoxypyrazine-2-carobxamide. The product was applied to a silica gel column chromatography and then developed using a mixture of chloroform and methanol of 9:1 volume ratio as eluting solution, whereby 0.8 g. of pure oily N-(2-diethylaminoethyl)-6-chloro-5-diethylamino-3-methoxypyrazine-2-carboxamide was obtained from the 2nd fraction.

| Elemental analysis for $C_{16}H_{28}N_5O_2Cl$: | | | |
|---|---|---|---|
| | C(%) | H(%) | N(%) |
| Calculated: | 53.70 | 7.89 | 19.57 |
| Found: | 53.46 | 7.55 | 19.71 |

EXAMPLE 15

To 5 ml. of isopropyl alcohol were added 390 mg. of methyl 6-chloro-3-methoxy-5-(4-methylpiperazinyl)-pyrazine-2-carboxylate and 350 mg. of N,N-diethylethylenediamine and the mixture was refluxed for 7 days After the reaction was over, the solvent was distilled off under reduced pressure from the reaction mixture and the residue obtained was dissolved in 20 ml. of chloroform. The solution was acidified with hydrochloric acid and extracted with 20 ml. of water. The extract was basified with aqeuous ammonia and then extracted three times each time with 2 ml. of chloroform. The extracts were combined, washed with water, dried, and then chloroform was distilled off under reduced pressure. The oily material obtained was triturated with 5 ml. of n-hexane to provide 250 mg. of yellow crystals of N-(2-diethylaminoethyl)-6-chloro-3-methoxy-5-(4-methyl-piperazinyl)pyrazine-2-carboxamide. The yellow plate crystals obtained by recrystallizing the product from n-hexane melted at 77°-78° C.

| Elemental analysis for $C_{17}H_{29}N_6O_2Cl$: | | |
|---|---|---|
| | C(%) | H(%) | N(%) |
| Calculated: | 53.05 | 7.59 | 21.83 |
| Found: | 52.94 | 7.64 | 21.67 |

Reference example 11: Production of 6-chloro-5-ethylamino-3-methoxypyrazine-2-carboxylic acid:

In a solution of 18.7 g. of sodium hydroxide in 400 ml. of water was suspended 104 g. of methyl 6-chloro-5-ethylamino-3-methoxypyrazine-2-carboxylate and the suspension was stirred for 15 hours at room temperature to give a homogeneous solution. The solution was acidified with 80 ml. of an aqueous 18% hydrochloric acid solution and then allowed to stand for 2 hours at 5°-10° C. The crystals formed were recovered by filtration, washed with water and dried over anhydrous phosphorous pentoxide under reduced pressure to provide 92.5 of 6-chloro-5-ethylamino-3-methoxypyrazine-2-carboxylic acid. Melting point 166.5°-166° C. (recrystallized from chloroform).

| Elemental analysis for $C_8H_{10}N_3O_3Cl$: | | |
|---|---|---|
| | C(%) | H(%) | N(%) |
| Calculated: | 41.48 | 4.35 | 18.14 |
| Found: | 41.47 | 4.34 | 17.87 |

Reference example 12: Production of 6-chloro-3-methoxy-5-methyl thiopyrazine-2-carboxylic acid:

A mixture of 3.56 g. of methyl 5,6-dichloro-3-methoxypyrazine-2-carboxylate, 15 ml. of an aqueous solution of 20% sodium methanethiolate and 30 ml. of ethanol was stirred for 2 hours at 70°-80° C. After cooling the mixture to room temperature and adding 80 ml. of water thereto, the mixture was acidfied with concentrated hydrochloric acid, whereby crystals were formed. The crystals were recovered by filtration washed with water and dried to provide 2.55 g. of colorless acicular crystals of 6-chloro-3-methoxy-5-methylthiopyrazine-2-carboxylic acid melting at 206°-207° C.

| Elemental analysis for $C_7H_7N_2O_3SCl$ | | |
|---|---|---|
| | C(%) | H(%) | N(%) |
| Calculated: | 35.83 | 3.01 | 11.94 |
| Found: | 36.05 | 2.98 | 11.82 |

Reference example 13: Production of 5-benzylamino-6-chloro-3-methoxypyrazine-2-carboxylic acid:

a. To 30 ml. of isopropyl alcohol were added 2.37 g. of methyl 5,6-dichloro-3-methoxypyrazine-2-carboxylate, 1.2 g. of benzylamine, and 1.4 ml. of triethylamine and the mixture was refluxed for 2 hours. The reaction mixture was cooled to room temperature, the solvent was distilled off under reduced pressure, and the residue obtained was washed three times each time with 30 ml. of water and dried to provide 2.95 g. of methyl 5-benzylamino-6-chloro-3-methoxypyrazine-2-carboxylate melting at 118°-119° C.

| Elemental analysis for $C_{14}H_{14}N_3O_3Cl$: | | |
|---|---|---|
| | C(%) | H(%) | N(%) |
| Calculated: | 54.64 | 4.59 | 13.65 |
| Found: | 54.34 | 4.57 | 13.37 | b. To a mixture of 13 ml. of a 0.5 N aqueous sodium hydroxide solution and 0.5 ml. of methanol was added 2.0 g. of methyl 5-benzylamino-6-chloro-3-methoxypyrazine-2-carboxylate and the mixture was heated to 90° C. for 10 minutes. The reaction mixture was cooled to room temperature and neutralized with hydrochloric acid, whereby crystals were formed. The crystals were recovered by filtration washed with water and dried to provide 1.85 g. of 5-benzylamino-6-chloro-3-methoxypyrazine-2-carboxylic acid melting at 189° C. (decomp.).

| Elemental analysis for $C_{13}H_{12}O_3N_3Cl$ | | |
|---|---|---|
| | C(%) | H(%) | N(%) |
| Calculated: | 53.16 | 4.12 | 14.31 |
| Found: | 52.80 | 4.10 | 14.03 |

Reference example 14: Production of 5-allylamino-6-chloro-3-methoxypyrazine-2-carboxylic acid:

a. To 30 ml. of isopropyl alcohol were added 2.37 g. of methyl 5,6-dichloro-3-methoxypyrazine-2-carboxylate, 0.8 ml of allylamine and 2.9 ml. of triethylamine and the mixture was refluxed for 2 hours. The reaction mixture was cooled to room temperature and the solvent was distilled off under reduced pressure from the reaction mixture. The residue obtained was washed three times each time with 30 ml. of water, and dried to provide 2.35 g. of the colorless prism crystals of methyl 5-allylamino-6-chloro-3-methoxypyrazine-2-carboxylate melting at 115°-116° C.

| Elemental analysis for $C_{10}H_{12}N_3O_3Cl$ | | |
|---|---|---|
| | C(%) | H(%) | N(%) |
| Calculated: | 46.61 | 4.69 | 16.31 |
| Found: | 46.45 | 4.69 | 15.93 | b. To 17 ml. of a 0.5 aqueous sodium hydroxide solution was added 2.35 g. of methyl 5-allylamino-6-chloro-3-methoxypyrazine-2-carboxylate and the mixture was heated to 80° C. for 10 minutes. The reaction mixture was cooled to room temperature and acidified with concentrated hydrochloric acid, whereby crystals were formed. The crystals were recovered by filtration washed with water and dried to provide 2.0 g. of 5-allylamino-6-chloro-3-methoxypyrazine-2-carboxylicacid melting at 125°-126° C (decomp).

| Elemental analysis for $C_9H_{10}N_3O_3Cl$ | | |
|---|---|---|
| | C(%) | H(%) | N(%) |
| Calculated: | 44.37 | 4.14 | 17.25 |
| Found: | 44.20 | 4.13 | 16.83 |

Reference example 15; Production of 6-chloro-3-methoxy-5-(o-methoxyphenoxy)pyrazine-2-carboxylic acid;

a. To 20 ml of a solution of 250 mg of metallic sodium in isopropylalcohol was added 1.24 g of o-methoxyphenol under ice cooling and the mixture was stirred at room temperature for 30 minutes. A solution of 2.37 g of methyl 5,6-dichloro-3-methoxypyrazine-2-carboxylate in 15 ml of isopropylalcohol was added dropwise to the solution at 10°-20° C over a period of 30 minutes. Then, the mixture was refluxed for 0.5 hour and dispersed in 100 ml of chilled water, whereby crystals were formed. The crystals were recovered by filtration to provide isopropyl 6-chloro-3-methoxy-5-(o-methoxyphenoxy) pyrazine carboxylate melting at 94°-95° C.

| Elemental analysis for $C_{16}H_{17}N_2O_5Cl$ | | | |
|---|---|---|---|
| | C(%) | H(%) | N(%) |
| Calculated: | 54.48 | 4.86 | 7.94 |
| Found: | 54.11 | 4.69 | 7.54 | b. To 50 ml. of a 0.2 aqueous sodium hydroxide solution was added 2.9 g. of isopropyl 6-chloro-3-methoxy-5-(o-methoxyphenoxy)pyrazine-2-carboxylate and the mixture was heated to 80° C. for 30 minutes. The reaction mixture was cooled to room temperature and acidified with concentrated hydrochloric acid, whereby crystals were formed. The crystals were recovered by filtration, washed with water and dried to provide 1.55 g. of 6-chloro-3-methoxy-5-(o-methoxyphenoxy)pyrazine-2-caroxylic acid melting at 165° C. (recrystallized from isopropylalcohol.

| Elemental analysis for $C_{13}H_{11}O_5N_2Cl$ | | | |
|---|---|---|---|
| | C(%) | H(%) | N(%) |
| Calculated: | 50.26 | 3.57 | 9.02 |
| Found: | 50.39 | 3.55 | 8.63 |

Reference example 16: Production of 5-amino-6-bromo-3-methoxypyrazine-2-carboxylic acid:

a. To 140 ml. of methanol were added 8.0 g. of methyl 5-amino-6-chloro-3-methoxypyrazine-2-carboxylate, 2.26 g. of magnesium oxide, and 5.1 g. of 5% palladium carbon and the mixture was hydrogenated at room temperature and atmospheric pressure. After absorbing a theoretical amount (900 ml.) of hydrogen, the insoluble materials were recovered by filtration and extracted with 200 ml. of a hot mixture of isopropyl alcohol and water in a 1 : 1 volume ratio. The extract was combined with the filtrate obtained above and the mixture was concentrated to 100 ml under reduced pressure and ice-cooled, whereby crystals were formed. The crystals were recovered by filtration to provide 5.0 g. of colorless plate crystals of methyl 5-amino-3-methoxypyrazine-2-carboxylate melting at 225°-226° C. (decomp.).

| Elemental analysis for $C_7H_9N_3O_3$: | | | |
|---|---|---|---|
| | C(%) | H(%) | N(%) |
| Calculated: | 45.90 | 4.95 | 22.94 |
| Found: | 45.76 | 4.97 | 22.94 | b. To 20 ml. of acetic acid was added 1.8 g. of methyl 5-amino-3-methoxypyrazine-2-carboxylate and then 10 ml. of acetic acid containing 0.56 ml. of bromine was added dropwise to the mixture at 50° C. over a period of 10 minutes. Then, the mixture was stirred for 10 minutes at 25°-30° C. and cooled to 12° C., whereby crystals were formed. The crystals were recovered by filtration and recrystallized from isopropyl alcohol to provide 1.85 g. of yellow prism crystals of methyl 5-amino-6-bromo-3-methoxypyrazine-2-carboxylate melting at 151°-152° C.

| Elemental analysis for $C_7H_8N_3O_3Br$: | | | |
|---|---|---|---|
| | C(%) | H(%) | N(%) |
| Calculated: | 32.08 | 3.08 | 16.03 |
| Found: | 32.00 | 3.05 | 15.90 | c. To 10 ml. of a 0.5 N aqueous sodium hydroxide solution was added 1.2 g. of methyl 5-amino-6-bromo-3-methoxypyrazine-2-carboxylate and the mixture was heated to 80° C. for 10 minutes. The reaction mixture was cooled to room temperature and acidified with hydrochloric acid, whereby crystals were formed. The crystals were recovered by filtration to provide 1.1 g. of 5-amino-6-bromo-3-methoxypyrazine-2carboxylic acid melting at 190°-195° C. (decomp.).

| Elemental analysis for $C_6H_6N_3O_3Br$: | | | |
|---|---|---|---|
| | C(%) | H(%) | N(%) |
| Calculated: | 29.05 | 2.44 | 16.94 |
| Found: | 28.81 | 2.40 | 16.68 |

Reference example 17: Production of 6-chloro-3,5-dimethoxypyrazine-2-carboxylic acid:

In 25 ml. of methanol was dissolved 7.1 g. of methyl 5,6-dichloro-3-metoxypyrazine-2-carboxylate and after adding to the solution a solution of 0.9 g. of metallic sodium in 25 ml. of methanol, the mixture was refluxed for one hour. The reaction mixture was cooled to room temperature and methanol was distilled off under reduced pressure. To the residue obtained was added 60 ml. of a 0.5 N aqueous sodium hydroxide solution and the mixture was stirred for 10 minutes st 80° C. The mixture was then cooled to room temperature and acidified with hydrochloric acid, whereby crystals were formed. The crystals were recovered by filtration, washed with water and dried to provide 5.5 g. of 6-chloro-3,5-dimethoxypyrazine-2-carboxylic acid melting at 195°-196° C. (recrystallized from a isopropyl alcohol-water mixture).

| Elemental analysis for $C_7H_7N_2O_4Cl$: | | | |
|---|---|---|---|
| | C(%) | H(%) | N(%) |
| Calculated: | 38.46 | 3.23 | 12.82 |
| Found: | 38.05 | 3.04 | 12.39 |

EXAMPLE 1

In 400 ml. of dichloromethane was suspended 43.5 g. of 6-chloro-5-ethylamino-3-methoxypyrazine-2-carboxylic acid and then 22.8 g. of triethylamine was added to the suspension to form a solution. After cooling the solution to temperatures of from −35° C. to −40° C., 21.4 g. of ethyl chlorocarbonate was added to the solution and the mixture was stirred for 2 hours at temperatures of from −25° C. to −30° C. Thereafter, 26.5 g of 2-aminomethyl-1-ethylpyrrolidine was added and the mixture was stirred for 2.5 hours at room temperature. The reaction mixture was then extracted in succession with 300 ml. of aqueous 4% hydrochloric acid, 170 ml. of aqueous 1% hydrochloric acid, and then 120 ml. of water. The extracts were combined, 2.5 g. of activated carbon was added thereto followed by filtering and the pH of the filtrate was adjusted to 12 with an aqueous 30% sodium hydroxide solution, whereby crystals were formed. The crystals were recovered by filtration, washed with water and a small amount of acetone, and dried to provide 57.2 g. of crude crystals of N-(1-ethyl-pyridine-2-ylmethyl)-6-chloro-5-ethylamino-3-methoxypyrazine-2-carboxamide. The crystals obtained by recrystallizing the product from isopropyl alcohol melted at 167.2° C.

The infrared absorption spectra of the product coincided with those of the product obtained in Example 11.

In 10 ml. of benzene was suspended 1.7 g. of the product and after adding to the suspension 1 g. of methyl iodide, the mixture was refluxed for 2 hours. The solvent was distilled off under reduce pressure and the residue obtained was recrystallized from a mixture of ethanol and water to provide 1.8 g. of N-(1-ethylpyrrolidin-2-ylmethyl)-6-chloro-5-ethylamino-3-methoxypyrazine-2-carboxamide methiodide melting at 204°–205° C. (decomp.).

| Elemental analysis for $C_{16}H_{27}N_5O_2ClI$: | | | |
|---|---|---|---|
| | C(%) | H(%) | N(%) |
| Calculated: | 39.72 | 5.63 | 14.48 |
| Found: | 39.64 | 5.65 | 14.34 |

EXAMPLE 17

To a mixture of 1.5 g. of benzylmercaptan, 0.58 g. of 50% oily sodium hydride, and 5 ml. of dimethylformamide was added 3.4 g. of N-(1-ethylpyrrolidin-2-ylmethyl)-6-chloro-5-ethylamino-3-methoxypyrazine-2-carboxamide and the mixture was stirred for 12 hours at room temperature. Then, the reaction mixture was dispersed in 100 ml. of ice water and extracted three times each time with 20 ml. of dichloromethane. The extracts were combined, dried over anhydrous potassium carbonate, and the solvent was distilled off under reduced pressure. The residue obtained was applied to an alumina column chromatography and purified using benzene at first and then the chloroform as eluting solution to provide 530 mg. of crystals of N-(1-ethylpyrrolidin-2-ylmethyl)-6-benzylthio-5-ethylamino-3-methoxypyrazine-2-carboxamide. The crystals obtained by recrystallizing the product from a mixture of benzene and n-hexane, melted at 95°–97° C.

| Elemental analysis for $C_{22}H_{31}N_5O_2S$ | | | |
|---|---|---|---|
| | C(%) | H(%) | N(%) |
| Calculated: | 61.51 | 7.27 | 16.30 |
| Found: | 61.83 | 7.24 | 15.87 |

EXAMPLE 18

In 30 ml. of methanol was dissolved 1.7 g. of N-(1-ethylpyrrolidin-2-ylmethyl)-6-chloro-5-ethylamino-3-methoxypyrazine-2-carboxamide and after adding to the solution 300 mg. of 5% palladium carbon, the hydrogenation was carried out at normal temperature and normal pressure. After a theoretical amount of hydrogen (120 ml.) was absorbed, the insoluble materials were filtered off and the solvent was distilled off from the filtrate under reduced pressure. The residue obtained was dissolved in 10 ml. of water and the solution was basified with an aqueous 20% sodium hydroxide solution, whereby crystals were formed. The crystals were recovered, washed with water, and recrystallized from acetone to provide 1.3 g. of N-(1-ethylpyrrolidin-2-ylmethyl)-5-ethylamino-3-methoxypyrazine-2-carboxamide melting at 139°–140° C.

| Elemental analysis for $C_{15}H_{25}N_5O_2$ | | | |
|---|---|---|---|
| | C(%) | H(%) | N(%) |
| Calculated: | 58.61 | 8.20 | 22.78 |
| Found: | 58.47 | 8.22 | 22.93 |

EXAMPLE 19

To 30 ml. of toluene were added 3.0 g. of methyl 6-chloro-5-ethylamino-3-methoxypyrazine-2-carboxylate and 3.0 g. of 2-aminomethyl-1-methylpyrrolidine and the mixture was refluxed for 4 days. The reaction mixture was acidified with hydrochloric acid at room temperature and then extracted twice each time with 30 ml. of water. From the toluene layer, 0.9 g. of methyl 6-chloro-5-ethylamino-3-methoxypyrazine-2-carboxylate used as the starting material was recovered. The extracts were combined, basified with aqueous ammonia and extracted three times each time with 30 ml. of chloroform. The extracts were combined and evaporated to dryness. By adding 50 ml. of ether to the residue formed, 1.0 g. of crystals of N-(1-methylpyrrolidin-2-ylmethyl)-6-chloro-5-ethylamino-3-methoxypyrazine-2-carboxamide were obtained. The colorless acicular crystals obtained by recrystallizing the product from a mixture of benzene and n-hexane melted at 126°–127° C.

| Elemental analysis for $C_{14}H_{22}N_5O_2Cl$: | | | |
|---|---|---|---|
| | C(%) | H(%) | N(%) |
| Calculated: | 51.30 | 6.76 | 21.36 |
| Found: | 51.45 | 6.87 | 21.01 |

The following pyrazine derivatives of formula III were produced by the following method:

Method A:

In 30 ml. of dichloromethane was suspended 0.01 mol of the pyrazine carboxylic acid derivative of formula I and then 0.011 mol of triethylamine was added to the suspension to form a solution. After cooling the solution to temperatures of from −20° C. to −40° C., 0.01 mol of ethyl chlorocarbonate was added to the solution and the mixture was stirred for 0.5 hours. Then, 0.01–0.013 mol of the amine derivative of formula II was added to the mixture at the same temperature followed by stirring for 0.5 hours and then the mixture was further stirred for 1-2 hours at room temperature. The reaction mixture was acidified with 1 N hydrochloric acid and then extracted three times each time with 30 ml. of water. The extracts were combined and neutralized with 1 N aqueous sodium hydroxide solution. In this case, when crystals were formed, the crystals were recovered by filtration, washed with water, dried, and recrystallized to provide the pure desired pyrazine carboxamide derivative of formula III. Also, when crystals did not form in this case, the neutralized extract was extracted three times each time with 30 ml. of dichloromethane. The extracts were combined, washed with water, dried, and the solvent was distilled off under reduced pressure. By purifying the residue obtained by recrystallization or an alumina or silicagel column chromatography, the pure desired pyrazine carboxamide derivative of formula III was obtained.

EXAMPLE 20

A method A described above 2.45 g. of N-(1-ethyl-pyrrolidin-2-ylmethyl)-6-chloro-3-methoxy-5-methyl-thiopyrazine-2-carboxamide having a melting point of 89°–90° C (recrystallized from n-hexane) was obtained from 2.34 g. of 6-chloro-3-methoxy-5-methylthiopyrazine-2-carboxylic acid and 1.35 g. of 2-aminomethyl-1-ethylpyrrolidine.

| Elemental analysis for $C_{14}H_{21}N_4O_2SCl$: | | | | |
|---|---|---|---|---|
| | C(%) | H(%) | N(%) | S(%) |
| Calculated: | 48.76 | 6.14 | 16.25 | 9.30 |
| Found: | 48.86 | 6.20 | 15.93 | 9.26 |

EXAMPLE 21

Following the procedure method A supra, 1.4 g. of N-(1-ethylpyrrolidin-2-ylmethyl)-5-benzylamino-6-chloro-3-methoxypyrazine-2-carboxamide melting at 145°–146° C. (recrystallized from a mixture of isopropylalcohol and n-hexane) was obtained from 1.75 g. of 5-benzylamino-6-chloro-3-methoxypyrazine-2-carboxylic acid and 0.8 g. of 2-aminomethyl-1-ethylpyrrolidine.

| Elemental analysis for $C_{20}H_{26}N_5O_2Cl$: | | | |
|---|---|---|---|
| | C(%) | H(%) | N(%) |
| Calculated: | 59.47 | 6.49 | 17.34 |
| Found: | 59.15 | 6.52 | 17.11 |

EXAMPLE 22

Following the procedure of method A supra, 1.81 g. of N-(1-ethylpyrrolidin-2-ylmethyl)-5-allylamino-6-chloro-3-methoxypyrazine-2-carboxamide melting at 164°–165° C. (recrystallized from a mixture of isopropylalcohol and n-hexane) was obtained from 1.7 g. of 5-allylamino-6-chloro-3-methoxypyrazine-2-carboxylic acid and 0.94 g. of 2-aminomethyl-1-ethylpyrrolidine.

| Elemental analysis for $C_{16}H_{24}N_5O_2Cl$ | | | |
|---|---|---|---|
| | C(%) | H(%) | N(%) |
| Calculated: | 54.31 | 6.84 | 19.79 |
| Found: | 54.30 | 6.86 | 19.27 |

EXAMPLE 23

Using the procedure of method A supra, 1.0 g. of colorless oily N-(1-ethylpyrroldin-2-ylmethyl)-6-chloro-3-methoxy-5-(o-methoxyphenoxy)pyrazine-2-carboxamide was obtained from 1.3 g. of 6-chloro-3-methoxy-5-(o-methoxyphenoxy)pyrazine-2-carboxylic acid and 0.57 g. of 2-aminomethyl-1-ethylpyrrolidine.

| Elemental analysis for $C_{20}H_{25}N_4O_4Cl$: | | | |
|---|---|---|---|
| | C(%) | H(%) | N(%) |
| Calculated: | 57.07 | 5.99 | 13.31 |
| Found: | 56.77 | 5.90 | 13.00 |

EXAMPLE 24

Using the procedure of method A supra, 1.1 g. of N-(1-ethoxypyrroldin-2-ylmethyl)-5-amino-6-bromo-3-methoxypyrazine-2-carboxamide melting at 153°–154° C. (recrystallized from a mixture of isopropyl alcohol and n-hexane) was obtained from 0.95 g. of 5-amino-6-bromo-3-methoxypyrazine-2-carboxylic acid and 0.52 g. of 2-aminomethyl-1-ethylpyrrolidine.

| Elemental analysis for $C_{13}H_{20}N_5O_2Br$: | | | |
|---|---|---|---|
| | C(%) | H(%) | N(%) |
| Calculated: | 43.59 | 5.63 | 19.55 |
| Found: | 43.61 | 5.58 | 19.15 |

EXAMPLE 25

Using the procedure of method A supra, 2.98 g. of N-(1-ethylpyrrolidin-2-ylmethyl)-6-chloro-3,5-dimethoxypyrazine-2-carboxamide melting at 100°–101° C. (recrystallized from n-hexane) was obtained from 3.28 g. of 6-chloro-3,5-dimethoxypyrazine-2-carboxylic acid and 2.03 g. of 2-aminomethyl-1-ethylpyrrolidine.

| Elemental analysis for $C_{14}H_{21}N_4O_3Cl$: | | | |
|---|---|---|---|
| | C(%) | H(%) | N(%) |
| Calculated: | 51.14 | 6.44 | 17.04 |
| Found: | 51.20 | 6.48 | 16.86 |

EXAMPLE 26

Using the procedure of method A supra, 1.0 g. of 6-chloro-5-ethylamino-3-methoxypyrazine-2-carboxylic acid (4-methyl)piperazide melting at 127°–128° C. (recrystallized from a mixture of benzene and n-hexane) was obtained from 1.09 g. of 6-chloro-5-ethylamino-3-methoxypyrazine-2-carboxylic acid and 0.6 g. of 1-methylpiperazine.

| Elemental analysis for $C_{13}H_{20}N_5O_2Cl$: | | | |
|---|---|---|---|
| | C(%) | H(%) | N(%) |
| Calculated: | 49.76 | 6.42 | 22.32 |
| Found: | 49.77 | 6.43 | 22.29 |

EXAMPLE 27

Using the procedure of method A supra, 0.8 g. of oily N-(2-diethylaminoethyl)-N-methyl-6-chloro-5-ethylamino-3-methoxypyrazine-2-carboxamide was obtained from 1.09 g. of 6-chloro-5-ethylamino-3-methoxypyrazine-2-carboxylic acid and 0.8 g. of N,N-diethyl-N'-methylethylenediamine.

| Elemental analysis for $C_{15}H_{26}N_5O_2Cl$ | | | |
|---|---|---|---|
| | C(%) | H(%) | N(%) |
| Calculated: | 52.40 | 7.62 | 20.37 |
| Found: | 52.56 | 7.68 | 20.14 |

EXAMPLE 28

Using the procedure method A supra, 2.2 g. of N-(3-diethylaminopropyl)-6-chloro-5-ethylamino-3-methoxypyrazine-2-carboxamide melting at 92°–94° C. (recrystallized from a mixture of benzene and n-hexane) was obtained from 2.2 g. of 6-chloro-5-ethylamino-3-methoxypyrazine-2-carboxylic acid and 1.6 g. of 3-diethylaminopropylamine.

| Elemental analysis for $C_{15}H_{26}N_5O_2Cl$ | | | |
|---|---|---|---|
| | C(%) | H(%) | N(%) |
| Calculated: | 52.40 | 7.62 | 20.37 |

| Elemental analysis for $C_{15}H_{26}N_5O_2Cl$ | | |
|---|---|---|
| | C(%) | H(%) | N(%) |
| Found: | 52.66 | 7.61 | 20.22 |

EXAMPLE 29

Using the procedure of method A, supra 2.5 g. of N-(2-piperidinoethyl)-6-chloro-5-ethylamino-3-methoxypyrazine-2-carboxamide having a melting point of 137°–139° C. (recrystallized from a mixture of benzene and n-hexane) was obtained from 2.3 g. of 6-chloro-5-ethylamino-3-methoxypyrazine-2-carboxylic acid and 1.43 g. of 2-piperidinoethylamine.

| Elemental analysis for $C_{15}H_{24}N_5O_2Cl$ | | |
|---|---|---|
| | C(%) | H(%) | N(%) |
| Calculated: | 52.70 | 7.08 | 20.49 |
| Found: | 52.76 | 6.98 | 19.83 |

EXAMPLE 30

Using the procedure of method A supra, 2.8 g. of N-[2-(N-methyl-N-phenylamino)ethyl]-6-chloro-5-ethylamino-3-methoxypyrazine-2-carboxamide melting at 138°–140° C. (recrystallized from a mixture of benzene and n-hexane) was obtained from 2.11 g. of 6-chloro-5-ethylamino-3-methoxypyrazine-2-carboxylic acid and 1.5 g. of N-methyl-N-phenylethylenediamine.

| Elemental analysis for $C_{17}H_{22}N_5O_2Cl$: | | |
|---|---|---|
| | C(%) | H(%) | N(%) |
| Calculated: | 56.12 | 6.09 | 19.25 |
| Found: | 55.90 | 6.07 | 18.98 |

EXAMPLE 31

Using the procedure of method A, supra, 1.6 g. of N-(2-morpholinoethyl)-6-chloro-5-ethylamino-3-methoxypyrazine-2-carboxamide melting at 119°–120° C. (recrystallized from a mixture of benzene and n-hexane) was obtained from 1.43 g. of 6-chloro-5-ethylamino-3-methoxypyrazine-2-carboxylic acid and 0.88 g. of 2-morpholinoethylamine.

| Elemental analysis for $C_{14}H_{22}N_5O_3Cl$ | | |
|---|---|---|
| | C(%) | H(%) | N(%) |
| Calculated: | 48.91 | 6.45 | 20.37 |
| Found: | 48.79 | 6.40 | 20.30 |

EXAMPLE 32

Using the procedure of method A supra, 1.3 g. of N-(1-cyclohexylpyrrolidin-2-ylmethyl)-6-chloro-5-ethylamino-3-methoxypyrazine-2-carboxamide melting at 164°–165° C. (recrystallized from toluene) was obtained from 2.3 g. of 6-chloro-5-ethylamino-3-methoxypyrazine-2-carboxylic acid and 1.8 g. of 2-aminomethyl-1-cyclohexylpyrrolidine.

| Elemental analysis for $C_{19}H_{30}N_5O_2Cl$: | | | |
|---|---|---|---|
| | C(%) | H(%) | N(%) | Cl(%) |
| Calculated: | 57.64 | 7.64 | 17.69 | 8.95 |
| Found: | 57.84 | 7.80 | 17.50 | 8.83 |

EXAMPLE 33

Using the procedure of method A supra, 2.2 g. of N-(1-cyclohexylpyrrolidin-3-yl)-6-chloro-5-ethylamino-3-methoxy pyrazine-2-carboxamide melting at 171°–173° C. (recrystallized from toluene) was obtained 2.3 g. of 6-chloro-5-ethylamino-3-methoxypyrazine-2-carboxylic acid and 1.7 g. of 3-amino-1-cyclohexylpyrrolidine.

| Elemental analysis for $C_{18}H_{28}N_5O_2Cl$: | | | |
|---|---|---|---|
| | C(%) | H(%) | N(%) | Cl(%) |
| Calculated: | 56.61 | 7.39 | 18.34 | 9.28 |
| Found: | 56.55 | 7.44 | 18.25 | 9.21 |

EXAMPLE 34

Using the procedure of method A supra, 2.9 g. of 6-chloro-5-ethylamino-3-methoxypyrazine-2-carboxylic acid (3-dimethylamino)piperidide melting at 78°–83° C. (recrystallized from a mixture of benzene and n-hexane) was obtained from 2.55 g. of 6-chloro-5-ethylamino-3-methoxypyrazine-2-carboxylic acid and 1.55 g. of 3-dimethylaminopiperidine.

| Elemental analysis for $C_{15}H_{24}N_5O_2Cl$: | | |
|---|---|---|
| | C(%) | H(%) | N(%) |
| Calculated: | 52.70 | 7.08 | 20.49 |
| Found: | 52.35 | 7.13 | 20.09 |

EXAMPLE 35

Using the procedure of method A, supra, 3 g. of N-[2-(N-benzyl-N-methylamino)ethyl]-6-chloro-5-ethylamino-3-methoxypyrazine-2-carboxamide melting at 119°–120° C. (recrystallized from a mixture of benzene and n-hexane) was obtained from 2.3 g. of 6-chloro-5-ethylamino-3-methoxypyrazine-2-carboxylic acid and 1.8 g. of N-benzyl-N-methylethylenediamine.

| Elemental analysis for $C_{18}H_{24}N_5O_2Cl$: | | |
|---|---|---|
| | C(%) | H(%) | N(%) |
| Calculated: | 57.21 | 6.40 | 18.53 |
| Found: | 57.01 | 6.45 | 18.46 |

EXAMPLE 36

In 20 ml. of methanol was dissolved 1.9 g. of N-[2-(N-benzyl-N-methyl amino)ethyl]-6-chloro-5-ethylamino-3-methoxypyrazine-2-carboxamide and after adding thereto 300 mg. of 5% palladium carbon, the hydrogenation was carried out at room temperature and atmospheric pressure. After absorbing 2 equivalents of hydrogen, the insoluble materials were filtered off and the filtrate was distilled under reduced pressure to remove the solvent. The residue obtained was recrystallized from a mixture of ether and ethanol to give 1.2 g. of N-[2-(methylamino)ethyl]-5-ethylamino-3-methoxypyrazine-2-carboxamide hydrochloride melting at 80° C.

| Elemental analysis for $C_{11}H_{19}N_5O_2Cl.3/2H_2O$: | | |
|---|---|---|
| | C(%) | H(%) | N(%) |
| Calculated: | 41.84 | 7.02 | 22.18 |
| Found: | 41.83 | 6.51 | 21.37 |

EXAMPLE 37

After cooling 54 ml. of a pyridine solution containing 2.7 g. of 2-aminomethyl-1-ethylpyrrolidine to −20° C., 7 ml. of a pyridine solution containing 0.7 g. of phosphorus trichloride was added dropwise to the solution and the mixture was stirred at room temperature for one hour. Then, 2.32 g. of 6-chloro-5-ethylamino-3-methoxypyrazine-2-carboxylic acid was added to the mixture and the resultant mixture was heated to 80° C. for 4 hours. After the reaction was over, the pyridine was distilled off under reduced pressure from the reaction mixture and the oily residue obtained was dissolved in 50 ml. of water. Activated carbon was added to the solution and then the mixture was filtered. Then, the filtrate was basified with 1.29 g. of sodium bicarbonate, the solution was concentrated upto about 20 ml., the pH of the concentrate was adjusted to 12 by adding an aqueous 20% sodium hydroxide solution, and then the concentrate was cooled by ice-water. The crystals formed were recovered by filtration to provide 2.46 g. of crude crystals of N-(1-ethylpyrrolidin-2-ylmethyl)-6-chloro-5-ethylamino-3-methoxypyrazine-2-carboxamide melting at 155°–160° C. The filtrate was extracted twice each time with 20 ml. of dichloromethane. The extracts were combined, dried over anhydrous potassium carbonate, the solvent was distilled off under reduced pressure, and the crystals thus formed were recovered by filtration to provide 0.12 g. of crude crystals of N-(1-ethylpyrrolidin-2-ylmethyl)-6-chloro-5-ethylamino-3-methoxypyrazine-2-carboxamide. The crystals thus obtained when recrystallized from isopropyl alcohol, point melted at 167.2° C. The infrared absorption spectra and the nuclear magnetic resonance spectra of the product were identical to those of the product obtained in Example 11.

EXAMPLE 38

In the same way as in Example 37, 2.92 g. of crude crystals of N-(2-diethyl aminoethyl)-6-chloro-5-ethylamino-3-methoxypyrazine-2-carboxamide melting at 130°–131° C. was obtained from 2.44 g. of N,N-diethylethylenediamine and 2.32 g. of 6-chloro-5-ethylamino-3-methoxypyrazine-2-carboxylic acid. The crystals obtained by recrystallizing the product from a mixture of benzene and n-hexane melted at 142° C. The infrared absorption spectra and nuclear magnetic resonance spectra of the product were identical to those of the product obtained in Example 6.

Reference Example 18

Production of methyl 3-methoxy-5,6-dimethylpyrazine-2-carboxylate:

a. In 40 ml of methanol there was suspended 3.8 g of 3-hydroxy-5,6-dimethylpyrazine-2-carboxylic acid, hydrogenchloride gas was introduced into the suspension for 2 hours under refluxing. The reaction mixture was concentrated to 20 ml under reduced pressure and ice-cooled, whereby crystals were formed. The crystals were recovered by filtration and dried to provide 3.0 g. of methyl 3-hydroxy-5,6-dimethylpyrazine-2-carboxylate. The colorless needle crystals obtained by recrystallizing the product from methanol melted at 156°–157° C.

| Elemental analysis for $C_8H_{10}N_2O_3$ | | | |
|---|---|---|---|
| | C(%) | H(%) | N(%) |
| Calculated: | 52.74 | 5.53 | 15.38 |
| Found: | 52.70 | 5.47 | 15.30 | b. To 8 ml. of phosphorus oxychloride containing one drop of concentrated sulfuric acid was added 2.4 g. of methyl 3-hydroxy-5,6-dimethylpyrazine-2-carboxylate and the mixture was refluxed for 7 hours. The excess phosphorus oxychloride was distilled off under reduced pressure from the reaction mixture and the residue obtained was dispersed in 20 ml. of ice water and the mixture was extracted three times each time with 20 ml. of ethyl acetate. The extracts were combined, dried over anhydrous magnesium sulfate, and then the solvent was distilled off to provide 1.9 g. of methyl 3-chloro-5,6-dimethylpyrazine-2-carboxylate. The colorless needle crystals obtained by recrystallizing from n-hexane melted at 50°–51° C.

| Elemental analysis for $C_8H_9N_2O_2Cl$ | | | |
|---|---|---|---|
| | C(%) | H(%) | N(%) |
| Calculated: | 47.89 | 4.52 | 13.96 |
| Found: | 47.55 | 4.50 | 13.71 | c. To 20 ml. of a solution of 0.1 g. metallic sodium in methanol was added 0.3 g. of methyl 3-chloro-5,6-dimethylpyrazine-2-carboxylate and the mixture was refluxed for one hour. The methanol was distilled off from the reaction mixture and the residue obtained was added to 20 ml. of water and the mixture was extracted three times each time with 20 ml. of dichloromethane. The extracts were combined, dried over anhydrous magnesium sulfate, and then the dichloromethane was distilled off to provide 0.2 g of methyl 3-methoxy-5,6-dimethylpyrazine-2-carboxylate. The yellow prism crystals obtained by recrystallizing from n-hexane melted at 80°–81° C.

| Elemental analysis for $C_9H_{12}N_2O_3$ | | | |
|---|---|---|---|
| | C(%) | H(%) | N(%) |
| Calculated: | 55.09 | 6.16 | 14.28 |
| Found: | 54.83 | 6.16 | 14.19 |

EXAMPLE 39

To 20 ml. of methanol there was added 10 g of methyl 3-methoxy-5,6-dimethylpyrazine-2-carboxylate and 1.5 g of 2-aminomethyl-1-ethylpyrrolidine and the mixture was refluxed for 30 hours. The methanol was distilled off under reduced pressure from the reaction mixture, the residue thus obtained was added to a mixture of 20 ml. of water and 20 ml of dichloromethane and mixed well. The organic layer that was separated was acidified with an aqueous hydrochloric acid and extracted three times each time with 20 ml. of water. The aqueous extracts were combined basified with a 2 N aqueous sodium hydroxide and extracted three times each time with 20 ml. of dichloromethane. The dichloromethane extracts were combined, dried over anhydrous magnesium sulfate and then the solvent was distilled off. The residue thus obtained was applied to a silica gel column chromatography and then developed using a mixture of chloroform and methanal in a 1:1 volume ratio as the eluting solution, whereby 0.8 g. of light yellow oily N-(1-ethylpyrrolidin-2-ylmethyl)-3-methoxy-5,6-dimethylpyrazine-2-carboxamide was obtained.

Elemental analysis for $C_{15}H_{24}N_4O_2$

|  | C(%) | H(%) | N(%) |
|---|---|---|---|
| Calculated: | 61.62 | 8.27 | 19.16 |
| Found: | 61.28 | 8.20 | 19.00 |

EXAMPLE 40 (TABLET)

| | |
|---|---|
| N-(1-ethylpyrrolidin-2-ylmethyl)-6-chloro-5-ethylamino-3-methoxypyrazine-2-carboxamide | 50 g. |
| Microcrystalline cellulose | 300 g. |
| Lactose | 200 g. |
| Calcium hydrogenphosphate | 200 g. |
| Corn starch | 100 g. |
| Magnesium stearate | 50 g. |

The above mixture was molded in a punch having a curvature of φ 6.5 mm. to make 10,000 tablets. If necessary, the tablets are coated with sugar by a conventional method.

EXAMPLE 41 (INJECTION)

| | |
|---|---|
| N-(1-ethylpyrrolidin-2-ylmethyl)-6-chloro-5-ethylamino-3-methoxypyrazine-2-carboxamide | 10 mg. |
| Hydrochloric acid | proper (pH 3.3) |
| Sodium chloride | 17 mg. |
| in ampule 2 ml. | |

The above mixture was dissolved in distilled water for injection and filled in ampule, sealed and sterilized.

We claim:

1. A pyrazine derivative represented by the formula

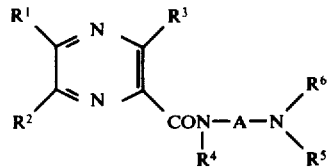

wherein $R^1$ and $R^2$, which may be the same or different, each represents a member selected from the group consisting of a hydrogen atom, a halogen atom, a hydroxy group, a $C_{1-4}$ alkoxy group, a phenyl $C_{1-4}$ alkoxy group, a phenoxy group, a mercapto group, a $C_{1-4}$ alkylthio group, a phenyl $C_{1-4}$ alkylthio group, a phenylthio group, an amino group, a substituted amino group selected from the group consisting of mono $C_{1-4}$ alkylamino, di $C_{1-4}$ alkylamino, hydroxy $C_{1-4}$ alkylamino, di $C_{1-4}$ alkylamino $C_{1-4}$ alkylamino, $C_{5-6}$ cycloalkylamino, $C_{2-4}$ alkenylamino, phenylamino, $C_{1-4}$ alkanoylamino, phenyl $C_{1-4}$ alkylamino, benzoylamino, pyrrolidino, piperidino, morpholino, piperazino and 4-$C_{1-4}$ alkylpiperazino, a $C_{1-4}$ alkyl group, a carbamoyl group, and a sulfamoyl group, $R^3$ represents a $C_{1-4}$ alkoxy group; $R^4$, $R^5$, and $R^6$, which may be the same or different, each represents a member selected from the group consisting of a hydrogen atom, a $C_{1-4}$ alkyl group, a $C_{5-6}$ cycloalkyl group, a phenyl $C_{1-4}$ alkyl group, and a phenyl group; and A repreents a $C_{1-4}$ alkylene group; said $R^4$ and A, $R^5$ and A, $R^4$ and $R^5$, or $R^5$ and $R^6$ may form together with the nitrogen atom a pyrrolidine, piperidine, piperazine, morpholine and imidazolidine ring and the pharmacologically acceptable non-toxic acid addition salts thereof.

2. A compound according to claim 1, which is a pyrazine derivative represented by the formula

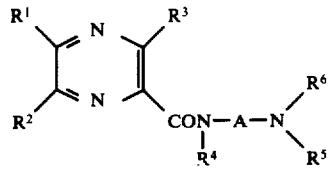

wherein $R^1$ represents an amino group or a substituted amino group selected from the group consisting of mono $C_{1-4}$ alkylamino, di $C_{1-4}$ alkylamino, hydroxy $C_{1-4}$ alkylamino, di $C_{1-4}$ alkylamino $C_{1-4}$ alkylamino, $C_{5-6}$ cycloalkylamino, $C_{2-4}$ alkenylamino, phenylamino, $C_{1-4}$ alkanoylamino, phenyl $C_{1-4}$ alkylamino, benzoylamino, pyrrolidino, piperidino, morpholino, piperazino and 4-$C_{1-4}$ alkylpiperazino; $R^2$ represents a halogen atom; $R^3$ represents a $C_{1-4}$ alkoxy group; $R^4$ represents a hydrogen atom or a $C_{1-4}$ alkyl group; $R^5$ and $R^6$, which may be the same or different, each represents a member selected from the group consisting of a hydrogen atom, a $C_{1-4}$ alkyl group, a $C_{5-6}$ cycloalkyl group, a phenyl $C_{1-4}$ alkyl group, and a phenyl group and, A repesents a $C_{1-4}$ alkylene group, said $R^4$ and A, $R^5$ and A, $R^4$ and $R^5$, or $R^5$ and $R^6$ may form together with the nitrogen atom a pyrrolidine, piperidine, piperazine, morpholine and imidazolidine ring and the pharmocologically acceptable non-toxic acid addition salts thereof.

3. A compound, according to claim 1, which is N-(1-Ethylpyrrolidin-2-ylmethyl)-5-ethylamino-6-chloro-3-methoxypyrazine-2-carboxamide.

4. A compound, according to claim 1, which is N-(1-Ethylpyrrolidin-2-ylmethyl)-5-amino-6-chloro-3-methoxypyrazine-2-carboxamide, 5. A compound, according to claim 1, which is N-(2-Diethylaminoethyl)-5-amino-6-chloro-3-methoxypyrazine-2-carboxamide.

6. A compound, according to claim 1, which is N-(1-Ethylpiperidin-3-yl)-5-amino-6-chloro-3-methoxypyrazine-2-carboxamide.

* * * * *